United States Patent
Awazu et al.

(10) Patent No.: US 8,034,597 B2
(45) Date of Patent: Oct. 11, 2011

(54) MICROORGANISM-DERIVED PSYCHROPHILIC ENDONUCLEASE

(75) Inventors: Naoyuki Awazu, Otsu (JP); Toshihiro Shodai, Otsu (JP); Hikaru Takakura, Otsu (JP); Masanari Kitagawa, Otsu (JP); Hiroyuki Mukai, Otsu (JP); Ikunoshin Kato, Otsu (JP)

(73) Assignee: Takara Bio Inc., Shiga (JP)

( * ) Notice: Subject to any disclaimer, the term of this patent is extended or adjusted under 35 U.S.C. 154(b) by 285 days.

(21) Appl. No.: 11/908,062

(22) PCT Filed: Mar. 8, 2006

(86) PCT No.: PCT/JP2006/304471
§ 371 (c)(1),
(2), (4) Date: Sep. 7, 2007

(87) PCT Pub. No.: WO2006/095769
PCT Pub. Date: Sep. 14, 2006

(65) Prior Publication Data
US 2009/0047705 A1 Feb. 19, 2009

(30) Foreign Application Priority Data
Mar. 8, 2005 (JP) ................................. 2005-064519

(51) Int. Cl.
*C12N 9/22* (2006.01)
(52) U.S. Cl. ........................................ 435/199; 435/183
(58) Field of Classification Search .................... None
See application file for complete search history.

(56) References Cited

U.S. PATENT DOCUMENTS

| 5,173,418 A | 12/1992 | Molin et al. |
| 6,479,260 B1 | 11/2002 | Takayama et al. |
| 2002/0042052 A1 | 4/2002 | Nilsen et al. |

FOREIGN PATENT DOCUMENTS

| WO | 9907887 A2 | 2/1999 |
| WO | 9927117 A1 | 6/1999 |
| WO | 0118230 A1 | 3/2001 |

OTHER PUBLICATIONS

Ngo et al., in The Protein Folding Problem and Tertiary Structure Prediction, 1994, Merz et al. (ed.), Birkhauser, Boston, MA, pp. 433 and 492-495.*
Office Action issued in corresponding Japanese Patent Application No. 2007-507147, mailed May 17, 2011, and English abstract of the Office Action.
Jekel et al., The periplasmic endonuclease I of *Escherichia coli* has amino-acid sequence homology to the extracellular DNases of *Vibrio cholerae* and *Aeromonas hydrophila*, Gene, 154:55-59 (1995).
Kulakova et al., Cold-active serine alkaline protease from the psychrotrophic bacterium *Shewanella* strain Ac10: Gene cloning and enzyme purification and characterization, Applied and Environmental Microbiology, 65(2)611-617 (1999).
Galkin et al., Cold-adapted alanine dehydrogenases from two antarctic bacterial strains: Gene cloning, protein characterization, and comparison with mesophilic and thermophilic counterparts, Applied and Environmental Microbiology, 65(9)4014-4020 (1999).
Nomenclature Committee of the International Union of Biochemistry and Molecular biology (http://www.chem.qmul.ac.uk/iubmb/enzyme/), 1981.
Furrer et al., Improving PCR efficiency, Nature, 324(346):6282 (1990).
Eaves et al., Isolation and properties of an exocellular nuclease of *Serratia marcescens*, J. Bacteriol., 85:273-278 (1963).
Stevens et al., Studies on a nuclease from *Azotobacter agilis*, The Journal of Biological Chemistry, 235(10) 3016-3022 (1960).

* cited by examiner

*Primary Examiner* — Richard Hutson
(74) *Attorney, Agent, or Firm* — Browdy and Neimark, PLLC

(57) ABSTRACT

A polypeptide having an endonuclease activity derived from a psychrophilic microorganism *Shewanella* sp. strain Ac10, which exhibits high activity at low temperatures, can remove any nucleic acid present in a protein solution and can reduce the viscosity of a protein extract; and a nucleic acid encoding the polypeptide.

2 Claims, 8 Drawing Sheets

SEQUENCE LISTING

<160> NUMBER OF SEQ ID NOS: 11

<210> SEQ ID NO 1
<211> LENGTH: 30
<212> TYPE: DNA
<213> ORGANISM: Artificial Sequence
<220> FEATURE:
<223> OTHER INFORMATION: A sequence of designed oligonucleotide PCR
      primer for amplifying a gene of encoding DNase. "nucleotide 4 to 9
      is EcoRI restriction site."

<400> SEQUENCE: 1
ggcgaattca tgtttttgtt aattttaggg                                    30

<210> SEQ ID NO 2

-continued

```
<211> LENGTH: 30
<212> TYPE: DNA
<213> ORGANISM: Artificial Sequence
<220> FEATURE:
<223> OTHER INFORMATION: A sequence of designed oligonucleotide PCR
      primer for amplifying a gene of encoding DNase. "nucleotide 4 to 9
      is BamHI restriction site."

<400> SEQUENCE: 2
gcgggatcct taacgaacta agccgttatt                                      30

<210> SEQ ID NO 3
<211> LENGTH: 254
<212> TYPE: PRT
<213> ORGANISM: Shewanella sp.

<400> SEQUENCE: 3
```

Met Phe Leu Leu Ile Leu Gly Phe Ile Leu Arg Leu Ser Ser Thr His
1               5                   10                  15

Ser Trp Leu Phe Gly Val Ser Leu Leu Cys Gly Ile Phe Ser Ser Thr
            20                  25                  30

Leu Ile Ala Ala Glu His Pro Ser Ser Phe Gly Lys Ala Lys Lys Val
        35                  40                  45

Ala Lys Lys Ile Tyr Gln Gln His Leu Pro Leu Ser Ser Phe Tyr Cys
    50                  55                  60

Gly Cys Asp Ile Ala Ile Ala Gly Lys Leu Trp Gln Ala Asp His Ala
65                  70                  75                  80

Ser Cys Gly Tyr Gln Val Arg Lys Gln Ile Ile Arg Ala Asn Arg Ile
                85                  90                  95

Glu Trp Glu His Val Val Pro Ala Trp Glu Phe Gly His Gln Leu Gln
            100                 105                 110

Cys Trp Gln Asp Gly Gly Arg Lys Asn Cys Gly Lys Asn Asn Lys Gln
        115                 120                 125

Phe Lys Lys Met Glu Ala Asp Leu His Asn Leu Val Pro Ala Val Gly
    130                 135                 140

Glu Val Asn Gly Asp Arg Ser Asn Phe Arg Phe Ser Asp Trp Gly Gly
145                 150                 155                 160

Lys Ala Asp Gln Tyr Gly Gln Cys Glu Met Ile Val Asp Phe Lys Gly
                165                 170                 175

Arg Lys Ala Gln Pro Pro Lys Arg Ala Arg Gly Pro Ile Ala Arg Thr
            180                 185                 190

Tyr Leu Tyr Met Gln Lys Ile Tyr Gly Leu Gln Ile Ser Ser Ser Gln
        195                 200                 205

Gln Lys Leu Phe Asn Ala Trp Asp Lys Met Gln Pro Val Thr Ala Thr
    210                 215                 220

Glu Cys Lys Arg Asp Thr Leu Ile Ala Ala Asn Gln Gly Asn His Asn
225                 230                 235                 240

Asp Phe Val Phe Lys Gln Cys Gln Asn Asn Gly Leu Val Arg
                245                 250

```
<210> SEQ ID NO 4
<211> LENGTH: 765
<212> TYPE: DNA
<213> ORGANISM: Shewanella sp.

<400> SEQUENCE: 4 atgttttgt taattttagg gtttattttg cgcttatcat ccacacactc ttggttattt    60
ggggtgtcgc ttctgtgcgg cattttttca tccacactta tcgcagcaga acatccaagt   120
```

```
agttttggta aagcgaaaaa agttgccaaa aagatttacc aacaacacct acctctcagt    180 tcctttatt gcggctgcga catcgccata gcaggcaaat tatggcaagc agatcatgct     240
agctgtggct atcaggttag aaaacaaatt attagagcca accgtattga atgggagcac    300 gtggttccg cttgggaatt tggtcatcaa ctgcaatgtt ggcaagatgg cggccgtaaa     360
aattgtggta aaacaacaa gcaattcaaa aaatggaag ccgatttaca taatctcgtt      420
cctgctgtcg gtgaggtcaa tggcgatcgc agcaactta ggtttagtga ttggggtgga    480
aaagcggatc aatacgggca atgtgaaatg attgtcgact ttaaaggccg caaagcacaa    540
ccgcctaaac gagcaagagg tcctattgct cgcacttacc tttatatgca aaaaatctat    600
ggtcttcaaa ttagcagcag tcagcaaaaa ttgtttaatg catgggacaa aatgcagcca    660
gtgacggcaa ctgagtgcaa gcgtgatacc ttaatcgctg ctaaccaagg taatcataat    720 gatttgtat tcaaacaatg ccaaaataac ggcttagttc gttaa                     765
```

<210> SEQ ID NO 5
<211> LENGTH: 271
<212> TYPE: PRT
<213> ORGANISM: Artificial Sequence
<220> FEATURE:
<223> OTHER INFORMATION: A sequence of artificial protein comprising
      Perfect DB sequence, His Tag sequence, Factor Xa sequence and
      linker, and DNase.

<400> SEQUENCE: 5

```
Met Asn His Lys Val His His His His His Ile Glu Gly Arg Asn
1               5                   10                  15

Ser Met Phe Leu Leu Ile Leu Gly Phe Ile Leu Arg Leu Ser Ser Thr
                20                  25                  30

His Ser Trp Leu Phe Gly Val Ser Leu Leu Cys Gly Ile Phe Ser Ser
            35                  40                  45

Thr Leu Ile Ala Ala Glu His Pro Ser Ser Phe Gly Lys Ala Lys Lys
        50                  55                  60

Val Ala Lys Lys Ile Tyr Gln Gln His Leu Pro Leu Ser Ser Phe Tyr
65                  70                  75                  80

Cys Gly Cys Asp Ile Ala Ile Ala Gly Lys Leu Trp Gln Ala Asp His
                85                  90                  95

Ala Ser Cys Gly Tyr Gln Val Arg Lys Gln Ile Ile Arg Ala Asn Arg
            100                 105                 110

Ile Glu Trp Glu His Val Val Pro Ala Trp Glu Phe Gly His Gln Leu
        115                 120                 125

Gln Cys Trp Gln Asp Gly Gly Arg Lys Asn Cys Gly Lys Asn Asn Lys
    130                 135                 140

Gln Phe Lys Lys Met Glu Ala Asp Leu His Asn Leu Val Pro Ala Val
145                 150                 155                 160

Gly Glu Val Asn Gly Asp Arg Ser Asn Phe Arg Phe Ser Asp Trp Gly
                165                 170                 175

Gly Lys Ala Asp Gln Tyr Gly Gln Cys Glu Met Ile Val Asp Phe Lys
            180                 185                 190

Gly Arg Lys Ala Gln Pro Pro Lys Arg Ala Arg Gly Pro Ile Ala Arg
        195                 200                 205

Thr Tyr Leu Tyr Met Gln Lys Ile Tyr Gly Leu Gln Ile Ser Ser Ser
    210                 215                 220

Gln Gln Lys Leu Phe Asn Ala Trp Asp Lys Met Gln Pro Val Thr Ala
225                 230                 235                 240

Thr Glu Cys Lys Arg Asp Thr Leu Ile Ala Ala Asn Gln Gly Asn His
```

```
                          245                 250                 255
Asn Asp Phe Val Phe Lys Gln Cys Gln Asn Asn Gly Leu Val Arg
            260                 265                 270
```

<210> SEQ ID NO 6
<211> LENGTH: 816
<212> TYPE: DNA
<213> ORGANISM: Artificial Sequence
<220> FEATURE:
<223> OTHER INFORMATION: A sequence of a gene encoding an artificial
      protein comprising Perfect DB sequence, His Tag sequence, Factor
      Xa sequence and linker, and DNase.

<400> SEQUENCE: 6

```
atgaatcaca aagtgcatca tcatcatcat catatcgaag gtaggaattc gatgttttg      60
ttaatttag ggtttatttt gcgcttatca tccacacact cttggttatt tggggtgtcg    120
cttctgtgcg gcattttttc atccacactt atcgcagcag aacatccaag tagttttggt    180
aaagcgaaaa aagttgccaa aaagatttac caacaacacc tacctctcag ttccttttat    240
tgcggctgcg acatcgccat agcaggcaaa ttatggcaag cagatcatgc tagctgtggc    300
tatcaggtta gaaaacaaat tattagagcc aaccgtattg aatgggagca cgtggttccc    360
gcttgggaat ttggtcatca actgcaatgt tggcaagatg gcggccgtaa aaattgtggt    420
aaaaacaaca agcaattcaa aaaaatggaa gccgatttac ataatctcgt tcctgctgtc    480
ggtgaggtca atggcgatcg cagcaacttt aggtttagtg attggggtgg aaaagcggat    540
caatacgggc aatgtgaaat gattgtcgac tttaaaggcc gcaaagcaca accgcctaaa    600
cgagcaagag gtcctattgc tcgcacttac ctttatatgc aaaaaatcta tggtcttcaa    660
attagcagca gtcagcaaaa attgtttaat gcatgggaca aaatgcagcc agtgacggca    720
actgagtgca agcgtgatac cttaatcgct gctaaccaag gtaatcataa tgattttgta    780
ttcaaacaat gccaaaataa cggcttagtt cgttaa                             816
```

<210> SEQ ID NO 7
<211> LENGTH: 30
<212> TYPE: DNA
<213> ORGANISM: Artificial Sequence
<220> FEATURE:
<223> OTHER INFORMATION: A sequence of designed oligonucleotide PCR
      primer for amplifying a gene of encoding DNase. "nucleotide 4 to 9
      is NdeI restriction site."

<400> SEQUENCE: 7

```
ggccatatga tgttttgtt aattttaggg                                      30
```

<210> SEQ ID NO 8
<211> LENGTH: 725
<212> TYPE: PRT
<213> ORGANISM: Artificial Sequence
<220> FEATURE:
<223> OTHER INFORMATION: A sequence of artificial protein comprising
      Perfect DB sequence, His Tag sequence, Trigger Factor sequence,
      HRV 3C sequence, Thrombin sequence, Factor Xa sequence and linker,
      and endonuclease.

<400> SEQUENCE: 8

```
Met Asn His Lys Val His His His His His His Met Gln Val Ser Val
1               5                   10                  15

Glu Thr Thr Gln Gly Leu Gly Arg Arg Val Thr Ile Thr Ile Ala Ala
            20                  25                  30

Asp Ser Ile Glu Thr Ala Val Lys Ser Glu Leu Val Asn Val Ala Lys
        35                  40                  45
```

```
Lys Val Arg Ile Asp Gly Phe Arg Lys Gly Lys Val Pro Met Asn Ile
     50                  55                  60
Val Ala Gln Arg Tyr Gly Ala Ser Val Arg Gln Asp Val Leu Gly Asp
 65                  70                  75                  80
Leu Met Ser Arg Asn Phe Ile Asp Ala Ile Ile Lys Glu Lys Ile Asn
                 85                  90                  95
Pro Ala Gly Ala Pro Thr Tyr Val Pro Gly Glu Tyr Lys Leu Gly Glu
                100                 105                 110
Asp Phe Thr Tyr Ser Val Glu Phe Glu Val Tyr Pro Glu Val Glu Leu
             115                 120                 125
Gln Gly Leu Glu Ala Ile Glu Val Glu Lys Pro Ile Val Glu Val Thr
             130                 135                 140
Asp Ala Asp Val Asp Gly Met Leu Asp Thr Leu Arg Lys Gln Gln Ala
145                 150                 155                 160
Thr Trp Lys Glu Lys Asp Gly Ala Val Glu Ala Glu Asp Arg Val Thr
                165                 170                 175
Ile Asp Phe Thr Gly Ser Val Asp Gly Glu Glu Phe Glu Gly Gly Lys
                180                 185                 190
Ala Ser Asp Phe Val Leu Ala Met Gly Gln Gly Arg Met Ile Pro Gly
            195                 200                 205
Phe Glu Asp Gly Ile Lys Gly His Lys Ala Gly Glu Glu Phe Thr Ile
210                 215                 220
Asp Val Thr Phe Pro Glu Glu Tyr His Ala Glu Asn Leu Lys Gly Lys
225                 230                 235                 240
Ala Ala Lys Phe Ala Ile Asn Leu Lys Lys Val Glu Glu Arg Glu Leu
                245                 250                 255
Pro Glu Leu Thr Ala Glu Phe Ile Lys Arg Phe Gly Val Glu Asp Gly
            260                 265                 270
Ser Val Glu Gly Leu Arg Ala Glu Val Arg Lys Asn Met Glu Arg Glu
            275                 280                 285
Leu Lys Ser Ala Ile Arg Asn Arg Val Lys Ser Gln Ala Ile Glu Gly
290                 295                 300
Leu Val Lys Ala Asn Asp Ile Asp Val Pro Ala Ala Leu Ile Asp Ser
305                 310                 315                 320
Glu Ile Asp Val Leu Arg Arg Gln Ala Ala Gln Arg Phe Gly Gly Asn
                325                 330                 335
Glu Lys Gln Ala Leu Glu Leu Pro Arg Glu Leu Phe Glu Glu Gln Ala
            340                 345                 350
Lys Arg Arg Val Val Val Gly Leu Leu Leu Gly Glu Val Ile Arg Thr
            355                 360                 365
Asn Glu Leu Lys Ala Asp Glu Glu Arg Val Lys Gly Leu Ile Glu Glu
            370                 375                 380
Met Ala Ser Ala Tyr Glu Asp Pro Lys Glu Val Ile Glu Phe Tyr Ser
385                 390                 395                 400
Lys Asn Lys Glu Leu Met Asp Asn Met Arg Asn Val Ala Leu Glu Glu
                405                 410                 415
Gln Ala Val Glu Ala Val Leu Ala Lys Ala Lys Val Thr Glu Lys Glu
            420                 425                 430
Thr Thr Phe Asn Glu Leu Met Asn Gln Gln Ala Ser Ala Gly Leu Glu
            435                 440                 445
Val Leu Phe Gln Gly Pro Ser Ala Gly Leu Val Pro Arg Gly Ser Gly
450                 455                 460
Gly Ile Glu Gly Arg His Met Met Phe Leu Leu Ile Leu Gly Phe Ile
```

|     |     |     |     | 465 |     |     |     |     | 470 |     |     |     |     | 475 |     |     |     |     | 480 |
| --- | --- | --- | --- | --- | --- | --- | --- | --- | --- | --- | --- | --- | --- | --- | --- | --- | --- | --- | --- |

Leu Arg Leu Ser Ser Thr His Ser Trp Leu Phe Gly Val Ser Leu Leu
                                485                 490                 495

Cys Gly Ile Phe Ser Ser Thr Leu Ile Ala Ala Glu His Pro Ser Ser
            500                 505                 510

Phe Gly Lys Ala Lys Lys Val Ala Lys Lys Ile Tyr Gln Gln His Leu
            515                 520                 525

Pro Leu Ser Ser Phe Tyr Cys Gly Cys Asp Ile Ala Ile Ala Gly Lys
        530                 535                 540

Leu Trp Gln Ala Asp His Ala Ser Cys Gly Tyr Gln Val Arg Lys Gln
545                 550                 555                 560

Ile Ile Arg Ala Asn Arg Ile Glu Trp Glu His Val Val Pro Ala Trp
                565                 570                 575

Glu Phe Gly His Gln Leu Gln Cys Trp Gln Asp Gly Gly Arg Lys Asn
                580                 585                 590

Cys Gly Lys Asn Asn Lys Gln Phe Lys Lys Met Glu Ala Asp Leu His
            595                 600                 605

Asn Leu Val Pro Ala Val Gly Glu Val Asn Gly Asp Arg Ser Asn Phe
        610                 615                 620

Arg Phe Ser Asp Trp Gly Gly Lys Ala Asp Gln Tyr Gly Gln Cys Glu
625                 630                 635                 640

Met Ile Val Asp Phe Lys Gly Arg Lys Ala Gln Pro Pro Lys Arg Ala
                645                 650                 655

Arg Gly Pro Ile Ala Arg Thr Tyr Leu Tyr Met Gln Lys Ile Tyr Gly
                660                 665                 670

Leu Gln Ile Ser Ser Ser Gln Gln Lys Leu Phe Asn Ala Trp Asp Lys
            675                 680                 685

Met Gln Pro Val Thr Ala Thr Glu Cys Lys Arg Asp Thr Leu Ile Ala
        690                 695                 700

Ala Asn Gln Gly Asn His Asn Asp Phe Val Phe Lys Gln Cys Gln Asn
705                 710                 715                 720

Asn Gly Leu Val Arg
                725

<210> SEQ ID NO 9
<211> LENGTH: 2175
<212> TYPE: DNA
<213> ORGANISM: Artificial Sequence
<220> FEATURE:
<223> OTHER INFORMATION: A sequence of a gene encoding an artificial
      protein comprising Perfect DB sequence, His Tag sequence, Trigger
      Factor sequence, HRV 3C sequence, Thrombin sequence, Factor Xa
      sequence and linker, and endonuclease.

<400> SEQUENCE: 9
atgaatcaca aagtgcatca tcatcatcat cacatgcaag tttcagttga aaccactcaa    60
ggccttggcc gccgtgtaac gattactatc gctgctgaca gcatcgagac cgctgttaaa   120
agcgagctgg tcaacgttgc gaaaaaagta cgtattgacg gcttccgcaa gggcaaagtg   180
ccaatgaata tcgttgctca gcgttatggc gcgtctgtac gccaggacgt tctgggtgac   240
ctgatgagcc gtaacttcat tgacgccatc attaagaaaa aaatcaatcc ggctggcgca   300
ccgacttatg ttccgggcga atacaagctg ggtgaagact tcacttactc tgtagagttt   360
gaagtttatc cggaagttga actgcaaggt ctggaagcga tcgaagttga aaaaccgatc   420
gttgaagtga ccgacgctga cgttgacggc atgctggata ctctgcgtaa acagcaggcg   480
acctggaaag aaaaagacgg cgctgttgaa gcagaagacc gcgtgaccat cgacttcacc   540

```
ggttctgtag acggcgaaga gttcgaaggc ggtaaagcgt ctgatttcgt actggcgatg    600
ggccagggtc gtatgatccc gggctttgaa gacggtatca aaggccacaa agctggcgaa    660
gagttcacca tcgacgtgac cttcccggaa gaataccacg cagaaaacct gaaaggtaaa    720
gcagcgaaat tcgctatcaa cctgaagaaa gttgaagagc gtgaactgcc ggaactgacc    780
gcagagttca tcaaacgttt cggcgttgaa gatggttccg tagaaggtct gcgcgctgaa    840
gtgcgtaaaa acatggagcg cgagctgaag agcgccatcc gtaaccgcgt taagtctcag    900
gcgatcgaag gtctggtaaa agctaacgac atcgacgtac cggctgcgct gatcgacagc    960
gaaatcgacg ttctgcgtcg ccaggctgca cagcgtttcg gtggcaacga aaacaagct    1020
ctggaactgc cgcgcgaact gttcgaagaa caggctaaac gccgcgtagt tgttggcctg    1080
ctgctgggcg aagttatccg caccaacgag ctgaaagctg acgaagagcg cgtgaaaggc    1140
ctgatcgaag agatggcttc tgcgtacgaa gatccgaaag aagttatcga gttctacagc    1200
aaaaacaaag aactgatgga caacatgcgc aatgttgctc tggaagaaca ggctgttgaa    1260
gctgtactgg cgaaagcgaa agtgactgaa aaagaaacca ctttcaacga gctgatgaac    1320
cagcaggcgt ccgcgggtct ggaagttctg ttccaggggc cctccgcggg tctggtgcca    1380
cgcggtagtg gtggtatcga aggtaggcat atgatgtttt tgttaatttt agggtttatt    1440
ttgcgcttat catccacaca ctcttggtta tttggggtgt cgcttctgtg cggcattttt    1500
tcatccacac ttatcgcagc agaacatcca agtagttttg gtaaagcgaa aaaagttgcc    1560
aaaaagattt accaacaaca cctacctctc agttcctttt attgcggctg cgacatcgcc    1620
atagcaggca aattatggca agcagatcat gctagctgtg ctatcaggt tagaaaacaa     1680
attattagag ccaaccgtat tgaatgggag cacgtggttc ccgcttggga atttggtcat    1740
caactgcaat gttggcaaga tggcggccgt aaaaattgtg gtaaaaacaa caagcaattc    1800
aaaaaaatgg aagccgattt acataatctc gttcctgctg tcggtgaggt caatggcgat    1860
cgcagcaact ttaggtttag tgattggggt ggaaaagcgg atcaatacgg caatgtgaa     1920
atgattgtcg actttaaagg ccgcaaagca caaccgccta acgagcaag aggtcctatt      1980
gctcgcactt acctttatat gcaaaaaatc tatggtcttc aaattagcag cagtcagcaa    2040
aaattgttta atgcatggga caaaatgcag ccagtgacgg caactgagtg caagcgtgat    2100
accttaatcg ctgctaacca aggtaatcat aatgattttg tattcaaaca atgccaaaat    2160
aacggcttag ttcgt                                                    2175
```

<210> SEQ ID NO 10
<211> LENGTH: 219
<212> TYPE: PRT
<213> ORGANISM: Shewanella sp.

<400> SEQUENCE: 10

Ala Glu His Pro Ser Ser Phe Gly Lys Ala Lys Val Ala Lys Lys
1               5                   10                  15

Ile Tyr Gln Gln His Leu Pro Leu Ser Ser Phe Tyr Cys Gly Cys Asp
            20                  25                  30

Ile Ala Ile Ala Gly Lys Leu Trp Gln Ala Asp His Ala Ser Cys Gly
        35                  40                  45

Tyr Gln Val Arg Lys Gln Ile Ile Arg Ala Asn Arg Ile Glu Trp Glu
    50                  55                  60

His Val Val Pro Ala Trp Glu Phe Gly His Gln Leu Gln Cys Trp Gln
65                  70                  75                  80

-continued

```
Asp Gly Gly Arg Lys Asn Cys Gly Lys Asn Asn Lys Gln Phe Lys Lys
             85                  90                  95
Met Glu Ala Asp Leu His Asn Leu Val Pro Ala Val Gly Glu Val Asn
            100                 105                 110
Gly Asp Arg Ser Asn Phe Arg Phe Ser Asp Trp Gly Gly Lys Ala Asp
            115                 120                 125
Gln Tyr Gly Gln Cys Glu Met Ile Val Asp Phe Lys Gly Arg Lys Ala
            130                 135                 140
Gln Pro Pro Lys Arg Ala Arg Gly Pro Ile Ala Arg Thr Tyr Leu Tyr
145                 150                 155                 160
Met Gln Lys Ile Tyr Gly Leu Gln Ile Ser Ser Ser Gln Lys Leu
            165                 170                 175
Phe Asn Ala Trp Asp Lys Met Gln Pro Val Thr Ala Thr Glu Cys Lys
            180                 185                 190
Arg Asp Thr Leu Ile Ala Ala Asn Gln Gly Asn His Asn Asp Phe Val
            195                 200                 205
Phe Lys Gln Cys Gln Asn Asn Gly Leu Val Arg
            210                 215
```

<210> SEQ ID NO 11
<211> LENGTH: 657
<212> TYPE: DNA
<213> ORGANISM: Shewanella sp.

<400> SEQUENCE: 11

```
gcagaacatc caagtagttt tggtaaagcg aaaaaagttg ccaaaaagat ttaccaacaa      60
cacctacctc tcagttcctt ttattgcggc tgcgacatcg ccatagcagg caaattatgg     120
caagcagatc atgctagctg tggctatcag gttagaaaac aaattattag agccaaccgt     180
attgaatggg agcacgtggt tcccgcttgg gaatttggtc atcaactgca atgttggcaa     240
gatggcggcc gtaaaaattg tggtaaaaac aacaagcaat tcaaaaaaat ggaagccgat     300
ttacataatc tcgttcctgc tgtcggtgag gtcaatggcg atcgcagcaa ctttaggttt     360
agtgattggg gtggaaaagc ggatcaatac gggcaatgtg aaatgattgt cgactttaaa     420
ggccgcaaag cacaaccgcc taaacgagca agaggtccta ttgctcgcac ttacctttat     480
atgcaaaaaa tctatggtct tcaaattagc agcagtcagc aaaaattgtt taatgcatgg     540
gacaaaatgc agccagtgac ggcaactgag tgcaagcgtg ataccttaat cgctgctaac     600
caaggtaatc ataatgattt tgtattcaaa caatgccaaa ataacggctt agttcgt       657
```

US 8,034,597 B2

MICROORGANISM-DERIVED PSYCHROPHILIC ENDONUCLEASE

TECHNICAL FIELD

The present invention relates to a polypeptide having an endonuclease activity which has a high activity at low-to-normal temperatures and is useful as a reagent for genetic engineering or an industrial enzyme, a nucleic acid encoding the polypeptide and a method for producing the polypeptide, as well as a method for degrading a nucleic acid and a method for reducing viscosity of a protein extract using the polypeptide.

BACKGROUND ART

Endonucleases are enzymes that are useful as reagents for genetic engineering, and are widely used for purposes including the following: elimination of genomic DNA prior to RT-PCR; reactions for degrading template DNA following RNA synthesis reactions using T7 or SP6 RNA polymerase; synthesis of DNA libraries; footprinting methods; elimination of nucleic acids from protein solutions; reduction in viscosity of protein extracts; and pretreatment of samples for two-dimensional electrophoresis.

Macromolecular nucleic acid-degrading enzymes (nucleases) are classified based on the modes of action as follows: (a) endonucleases which hydrolyze internal phosphodiester bonds of sugar phosphate chains (main chains) of macromolecular nucleic acids; and (b) exonucleases which successively cleave from 5' and/or 3' ends of main chains.

Endonucleases can be further classified based on their substrates as follows: (a) deoxyribonucleases (DNases) which degrade DNA; (b) ribonucleases (RNases) which degrade RNA; and (c) enzymes that degrade DNA and RNA (which may be simply called nucleases).

Among the endonucleases, deoxyribonucleases (a) are exemplified by the following: (i) deoxyribonuclease I (DNase I) which acts on double-stranded DNA and single-stranded DNA to degrade them into oligonucleotides each having a 3'—OH end and a 5'—P end; (ii) deoxyribonuclease II (DNase II) which acts on double-stranded DNA and single-stranded DNA to degrade them into oligonucleotides each having a 3'—P end and a 5'—OH end; (iii) endodeoxyribonuclease IV which selectively cleaves phosphodiester bonds on the 5' side of cytosines in single-stranded DNA molecules to degrade it into oligonucleotides each having a 3'—OH end and a 5'—P end; and (iv) restriction endonucleases (restriction enzymes) which recognize and cleave specific nucleotide sequences.

For example, the following is known about deoxyribonuclease I which is classified under EC 3.1.21.1 (see, for example, Non-patent Document 1) in addition to the above-mentioned activity: it has an activity of hydrolyzing phosphodiester bonds at distinct sites on two strands of double-stranded DNA to cause cleavage of single strands (nicking), resulting in gradual conversion of a macromolecular nucleic acid into smaller molecules; its reaction velocity varies depending on substrates and declines in the following order: double-stranded DNA>single-stranded DNA>oligonucleotide; and it has no or very low specificity for a nucleotide sequence.

It has been confirmed that deoxyribonuclease I exists in pancreas, kidney, liver, heart and blood of human, bovine, pig, sheep, rat, mouse, rabbit, chicken and fish, bacteria of the genus *Streptococcus*, *Escherichia coli*, T4 phage, λ phage and the like.

Deoxyribonuclease I is utilized for preventing false positive (pseudopositive) results in nucleic acid amplification reactions.

Deoxyribonuclease I is used as follows. DNase I is added before template DNA and DNA polymerase are added to a PCR reaction system in order to degrade contaminating nucleic acids, nucleic acids nonspecifically bound to primers and the like (see, for example, Non-patent Document 2).

It is necessary to inactivate deoxyribonuclease I before carrying out PCR. In order to inactivate deoxyribonuclease I which has the activity even at high temperatures, one must boil it for 30 minutes.

Methods using enzymes that exhibit their activities at low-to-normal temperatures and are readily inactivated at moderately high temperatures have been developed in order to solve the problems.

For example, it is described in Patent Document 1 that the DNase derived from shrimp (*Pandalus borealis*) does not exhibit its activity at 12° C. but exhibits the activity at 22 to 37° C. This enzyme cannot degrade single-stranded DNA. It is necessary to hold the enzyme at 94° C. for 5 minutes in order to completely inactivate it.

DNases and proteases derived from microorganisms isolated from seawater or marine organisms are described in Patent Document 2. The DNases exhibit their activities at 20° C. or above and inactivated at 50 to 60° C. or above although the thermosensitivity may vary more or less depending on the microorganisms from which they are derived. Although it is described therein that the DNases degrade double-stranded DNA, it is not described whether or not they degrade single-stranded DNA. No disclosure is contained therein concerning their physical and chemical properties except the thermosensitivity, the amino acid sequences, or the nucleotide sequences of nucleic acids encoding the DNases.

Among the endonucleases, endonucleases having activities of degrading DNA and RNA (c) are enzymes that are useful as reagents for genetic engineering. Furthermore, they are used for purposes including the following: elimination of nucleic acids from protein solutions; reduction in viscosity of protein extracts; and pretreatment of samples for two-dimensional electrophoresis.

For example, *Serratia marcescens* nuclease (see, for example, Patent Document 3 and Non-patent Document 3), silkworm nuclease SW, mung bean nuclease, potato nuclease and *Azotobacter agilis* nuclease (see, for example, Non-patent Document 4) are known. As to their reaction mechanisms, they specifically cleave intramolecular phosphodiester bonds in double-stranded DNA, single-stranded DNA and synthetic polynucleotides to generate 5'-dinucleotides and 5'-trinucleotides.

Among endonucleases having the above-mentioned activities, ones that act on all types of DNA and RNA substrates regardless of the forms (single-stranded, double-stranded, etc.) are used for elimination of nucleic acids from protein solutions, reduction in viscosity of protein extracts, or pretreatment of samples for two-dimensional electrophoresis (see, for example, Patent Document 3). For example, Benzonase (registered trademark) Nuclease from Novagen is used for this purpose.

An endonuclease having the above-mentioned activity can be used by adding it to a cell homogenate supernatant in order to reduce viscosity of a protein extract. When the protein of interest is extracted by cell disruption, the protein may be denatured due to heat generated during disruption or mechanical force, leading to decrease in the activity. Thus, cell disruption is generally carried out using an ice-cold buffer or cooling on ice in order to prevent the denaturation. In addition, it is necessary to cool the extract after disruption of course in cases where the protein of interest is thermolabile and also for suppressing the action of proteolytic enzymes in the extract.

An extract obtained from a rapidly growing cell (e.g., a microorganism) contains a large amount of nucleic acid materials. It is important to reduce the viscosity of the extract for facilitating subsequent sample processing.

Thus, it is necessary to reduce viscosity of a cooled cell extract. Furthermore, it is necessary to develop an endonuclease that exhibits the above-mentioned activity at low-to-normal temperatures for avoiding influence on the protein of interest if the protein of interest is thermolabile.

No endonuclease is known to retain an activity of degrading DNA and RNA even at low temperatures.

Patent Document 1: WO 99/07887
Patent Document 2: WO 01/18230
Patent Document 3: U.S. Pat. No. 5,173,418
Non-patent Document 1: Nomenclature Committee of the International Union of Biochemistry and Molecular Biology (http://www.chem.qmul.ac.uk/iubmb/enzyme/)
Non-patent Document 2: Furrer, B. et al., Nature, 346 (6282):324 (1990)
Non-patent Document 3: Eaves, George N. et al., J. Bacteriol., 85:273-278 (1963)
Non-patent Document 4: Stevens, Audrey et al., J. Biol. Chem., 235:3016-3022, 3023-3027 (1960)

DISCLOSURE OF INVENTION

Problems to be Solved by the Invention

The main object of the present invention is to provide a polypeptide having an endonuclease activity and a nucleic acid encoding the polypeptide. The polypeptide is useful as a reagent for genetic engineering or an industrial enzyme, and is useful for the following: elimination of genomic DNA; reactions for degrading template DNA following RNA synthesis reactions; synthesis of DNA libraries; footprinting methods; elimination of nucleic acids from protein solutions; reduction in viscosity of protein extracts; pretreatment of samples for two-dimensional electrophoresis; and pretreatment upon virus purification.

A further object of the present invention is to provide a method for producing the polypeptide having an endonuclease activity, as well as a method for degrading a nucleic acid and a method for reducing viscosity of a protein extract using the polypeptide having an endonuclease activity.

Means to Solve the Problems

As a result of intensive studies, the present inventors have found a nucleic acid encoding an endonuclease that has an activity at low temperatures from a psychrophilic microorganism *Shewanella* sp. strain Ac10, and produced the endonuclease polypeptide by cloning the gene. Thus, the present invention has been completed.

The first aspect of the present invention relates to a polypeptide having an endonuclease activity, which is selected from the group consisting of the following (a) to (e):
(a) a polypeptide having the amino acid sequence of SEQ ID NO:10 or a part thereof;
(b) a polypeptide having an amino acid sequence in which 1 or several amino acid(s) is(are) substituted, deleted, inserted or added in the amino acid sequence of SEQ ID NO:10 or a part thereof;
(c) a polypeptide having an amino acid sequence that shares at least 60% sequence homology to the amino acid sequence of SEQ ID NO:10;
(d) a polypeptide having an amino acid sequence encoded by the nucleotide sequence of SEQ ID NO:11; and
(e) a polypeptide having an amino acid sequence encoded by a nucleotide sequence that is capable of hybridizing to a complementary strand of the nucleotide sequence of SEQ ID NO:11 under stringent conditions.

The second aspect of the present invention relates to the polypeptide of the first aspect, which has at least the following physical and chemical properties (a) and (b):
(a) substrate specificity: acting on linear double-stranded DNA, circular double-stranded DNA, single-stranded DNA and RNA; and
(b) reactivity at low temperatures: retaining, at 0 to 10° C., 30% or more of its activity at 20° C.

The third aspect of the present invention relates to a nucleic acid encoding a polypeptide having an endonuclease activity, the nucleic acid being selected from the group consisting of the following (a) to (h):
(a) a nucleic acid encoding the amino acid sequence of SEQ ID NO:10 or a part thereof;
(b) a nucleic acid encoding an amino acid sequence in which 1 or several amino acid(s) is(are) substituted, deleted, inserted or added in the amino acid sequence of SEQ ID NO:10 or a part thereof;
(c) a nucleic acid encoding an amino acid sequence that shares at least 60% sequence homology to the amino acid sequence of SEQ ID NO:10;
(d) a nucleic acid having the nucleotide sequence of SEQ ID NO:11 or a part thereof;
(e) a nucleic acid having a nucleotide sequence in which 1 or several nucleotide(s) is(are) substituted, deleted, inserted or added in the nucleotide sequence of SEQ ID NO:11 or a part thereof;
(f) a nucleic acid that is capable of hybridizing to the nucleic acid of any one of (a) to (e) or a complementary strand thereof under stringent conditions;
(g) a nucleic acid having a nucleotide sequence that is different from the nucleotide sequence of the nucleic acid of any one of (a) to (f) due to degeneracy; and
(h) a nucleic acid having a nucleotide sequence that shares at least 60% sequence homology to the nucleotide sequence of the nucleic acid of any one of (a) to (g).

The fourth aspect of the present invention relates to a recombinant DNA that contains the nucleic acid of the third aspect.

The fifth aspect of the present invention relates to a transformant that harbors the nucleic acid of the third aspect.

The sixth aspect of the present invention relates to a method for producing a polypeptide having an endonuclease activity, the method comprising:
culturing the transformant of the fifth aspect; and
collecting a polypeptide having an endonuclease activity from the culture.

The seventh aspect of the present invention relates to a method for degrading a nucleic acid, the method comprising degrading a nucleic acid using the polypeptide of the first aspect.

The eighth aspect of the present invention relates to a method for reducing viscosity of a protein extract, the method comprising treating a protein extract using the polypeptide of the first aspect.

Effects of the Invention

The present invention provides a polypeptide having an endonuclease activity and a nucleic acid encoding the polypeptide as well as a method for producing the polypeptide having an endonuclease activity. The polypeptide is useful as a reagent for genetic engineering or an industrial enzyme, and is useful for the following: elimination of genomic DNA; reactions for degrading template DNA following RNA synthesis reactions; synthesis of DNA libraries; footprinting methods; elimination of nucleic acids from protein solutions; reduction in viscosity of protein extracts; pretreatment of samples for two-dimensional electrophoresis; and pretreatment upon virus purification. For example, the polypeptide having an endonuclease activity of the present invention can be preferably used for pretreatment for nucleic acid amplification reaction, processing of template nucleic acid following RNA synthesis, pretreatment of protein extracts and purification by elimination of nucleic acid from protein solutions.

BRIEF DESCRIPTION OF DRAWINGS

FIG. 13-1 illustrates results of examination for influence of various additives on the endonuclease of the present invention.

FIG. 13-2 illustrates results of examination for influence of various additives on the endonuclease of the present invention.

FIG. 13-3 illustrates results of examination for influence of various additives on the endonuclease of the present invention.

FIG. 13-4 illustrates results of examination for influence of various additives on the endonuclease of the present invention.

BEST MODE FOR CARRYING OUT THE INVENTION

Figure 1:
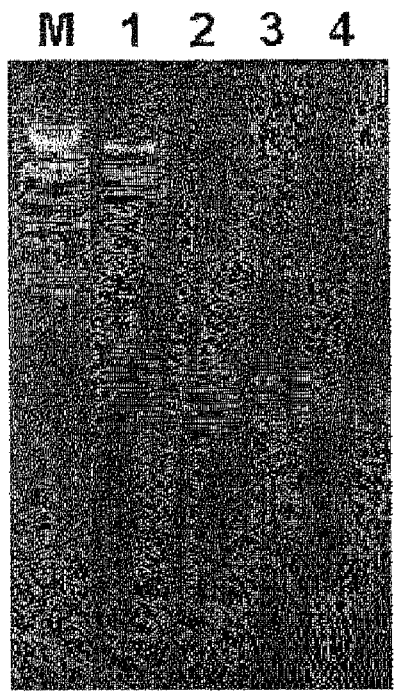
FIG. 1 illustrates results of activity measurement test for a psychrophilic microorganism-derived DNase.

As used herein, a polypeptide having an endonuclease activity refers to a polypeptide that catalyzes a reaction of hydrolyzing internal phosphodiester bonds of sugar phosphate chains (main chains) of macromolecular nucleic acids.

As used herein, a DNase refers to a polypeptide that catalyzes a reaction of acting on double-stranded DNA and single-stranded DNA to degrade them into oligonucleotides each having a 3'—OH end and a 5'—P end.

As used herein, a low temperature refers to a temperature lower than 20° C.; a normal (medium) temperature refers to a temperature within a range of 20 to 50° C.; and a high temperature refers to a temperature higher than 50° C.

The present invention is described in detail below.

(1) The Polypeptide Having an Endonuclease Activity of the Present Invention and a Nucleic Acid Encoding the Polypeptide The polypeptide having an endonuclease activity of the present invention may consist of the amino acid sequence of SEQ ID NO:10 or 3, or it may be a functional equivalent that has an activity substantially equivalent thereto.

According to the present invention, "functional equivalents" include a polypeptide having an amino acid sequence in which 1 or more, for example 1 or several, more specifically 1 to 10 amino acid residue(s) is(are) substituted, deleted, inserted or added in the amino acid sequence of SEQ ID NO:10 or 3.

A polypeptide having an endonuclease activity that shares at least 60%, preferably 70%, more preferably 80%, still more preferably 90% homology to the amino acid sequence of the polypeptide disclosed herein (SEQ ID NO:10 or 3) is within the scope of the present invention.

When a polypeptide is to be produced using genetic engineering techniques, it is often expressed as a fusion polypeptide. For example, an N-terminal peptide chain derived from another polypeptide may be attached at the N terminus of the polypeptide of interest in order to increase the expression level of the polypeptide. In another case, an appropriate peptide chain is attached at the N terminus or the C terminus of the polypeptide of interest. The polypeptide is then expressed, and the purification of the polypeptide of interest is facilitated by using a carrier having an affinity for the peptide chain. A polypeptide that has an endonuclease activity and an amino acid sequence partially different from that of the polypeptide having an endonuclease activity of the present invention is within the scope of the present invention as "a functional equivalent" provided that it exhibits an activity essentially equivalent to the polypeptide having an endonuclease activity of the present invention.

Nucleic acids encoding the polypeptide having an endonuclease activity of the present invention include a nucleic acid containing a nucleotide sequence encoding the amino acid sequence of SEQ ID NO:10 or 3, or a part thereof (e.g., a nucleic acid containing the nucleotide sequence of SEQ ID NO:11 or 4, or a part thereof). A nucleic acid encoding a polypeptide having an endonuclease activity that consists of an amino acid sequence in which 1 or more, for example 1 or several, more specifically 1 to 10 amino acid(s) is(are) substituted, deleted, inserted or added in the amino acid sequence of SEQ ID NO:10 or 3 is also included.

Also, a nucleotide sequence encoding a polypeptide having an endonuclease activity that is capable of hybridizing to such a sequence or a complementary strand thereof under stringent conditions is within the scope of the present invention. Although it is not intended to limit the present invention, "capable of hybridizing under stringent conditions" means that hybridization to the nucleic acid of the present invention or a complementary strand thereof is maintained after incubation in 6×SSC (1×SSC: 0.15 M NaCl, 0.015 M sodium citrate, pH 7.0) containing 0.5% SDS, 0.1% bovine serum albumin, 0.1% polyvinylpyrrolidone, 0.1% Ficoll 400 and 0.01% denatured salmon sperm DNA at 65° C. for 12 to 20 hours followed by washing in 2×SSC containing 0.5% SDS at 65° C. for 30 minutes.

A nucleic acid that shares at least 60%, preferably 70%, more preferably 80%, still more preferably 90% homology to the nucleotide sequence disclosed herein (SEQ ID NO:11 or 4) is within the scope of the present invention.

The homology can be determined using, for example, a computer program DNASIS-Mac (Takara Bio), a computer algorithm FASTA (version 3.0; Pearson, W. R. and Lipman, D. J., Pro. Natl. Acad. Sci. USA, 85(8):2444-2448 (1988)) or a computer algorithm BLAST (version 2.0; Altschul, S. F. et al., Nucleic Acids Res., 25(17):3389-3402 (1997)).

A nucleic acid having a nucleotide sequence that is different from the nucleotide sequence of the nucleic acid encoding a polypeptide having an endonuclease activity of the present invention due to degeneracy is within the scope of the present invention.

The expression "a nucleic acid containing a nucleotide sequence encoding an amino acid sequence" as used herein is explained below. It is known that one to six codon(s) (a combination of three nucleotides), which defines an amino acid in a gene, is assigned for each amino acid. Thus, many nucleic acids can encode a certain amino acid sequence although it depends on the amino acid sequence.

A nucleic acid that does not have a nucleotide sequence identical to the nucleotide sequence disclosed herein is encompassed by the present invention as long as it encodes the amino acid sequence disclosed herein.

The nucleic acid of the present invention may be DNA, RNA or chimeric nucleotide composed of DNA and RNA as long as it encodes the polypeptide having an endonuclease activity of the present invention. It may comprise a modified nucleotide. The nucleic acid may be in a double-stranded or single-stranded form.

The polypeptide having an endonuclease activity of the present invention is a polypeptide that retains a higher endonuclease activity at low temperatures as compared with Benzonase Nuclease (Novagen), a nuclease from *Serratia marcescens*.

The following physical and chemical properties (a) to (l) are those of the polypeptide having an endonuclease activity that consists of: the amino acid sequence of SEQ ID NO:10; an amino acid sequence encoded by a nucleic acid containing the nucleotide sequence of SEQ ID NO:11 or a part thereof; or an amino acid sequence in which 1 or more, for example 1 or several, more specifically 1 to 10 amino acid(s) is(are) substituted, deleted, inserted or added in the amino acid sequence of SEQ ID NO:10:

(a) substrate specificity: exhibiting its activity on linear double-stranded DNA, circular double-stranded DNA, single-stranded DNA and RNA;

(b) reactivity at low temperatures: retaining, at 0 to 10° C., 30% or more of its activity at 20° C.;

(c) range of temperatures at which it has the activity: 0 to 50° C.;

(d) pH stability: retaining its activity at pH ranging from 6 to 10 upon treatment at 37° C. for 30 minutes;

(e) molecular weight: 25 to 31 kDa as determined by SDS-PAGE;

(f) optimal magnesium ion concentration: 60 to 120 mM;

(g) optimal sodium ion concentration: 0 to 167 mm;

(h) optimal potassium ion concentration: 0 to 167 mm;

(i) optimal calcium ion concentration: 0 to 42 mm;

(j) optimal dithiothreitol concentration: 0 to 167 mM;

(k) optimal 2-mercaptoethanol concentration: 0 to 333 mM; and (l) optimal ammonium sulfate concentration: 0 to 83 mM.

Although there is no specific limitation concerning the polypeptide having an endonuclease activity of the present invention as long as it has the above-mentioned physical and chemical properties, the polypeptide can be obtained, for example, from *Shewanella* sp. strain Ac10.

Based on the analyzed biochemical characteristics, the polypeptide having an endonuclease activity of the present invention is suitable for elimination of nucleic acids from protein solutions and reduction in viscosity of protein extracts. In particular, the polypeptide is suitable for these uses at low temperatures.

According to the present invention, reactivity at a low temperature can be calculated as follows.

First, the amount of the polypeptide having an endonuclease activity of interest in enzyme unit is determined. For example, the amount of enzyme that increases absorbance at 260 nm by 0.001 in 1 minute at 37° C. in the following reaction system is defined as 1 U. In the reaction system, salmon testis DNA (Wako Pure Chemical Industries) is used as a substrate, and 100 μl of a sample of a polypeptide having an endonuclease activity is added to 500 μl of a substrate solution (40 μg/ml; 100 mM tris-hydrochloride buffer (pH 7.5) and 5 mM magnesium chloride).

Next, 100 μl of a solution containing a polypeptide having an endonuclease activity (2.3 U as determined according to the above-mentioned method) in 10 mM tris-hydrochloride buffer (pH 7.5) and 10 mM magnesium chloride is added to 500 μl of the substrate solution to prepare a reaction mixture.

The activity is calculated based on increase in absorbance at 260 nm determined after reacting the reaction mixture for 10 minutes at a temperature of 0, 5, 10, 15 or 20° C.

Then, the reactivity at low temperatures can be assessed by comparing the calculated relative activities (%) at the respective temperatures defining the endonuclease activity at 20° C. as 100.

For example, the relative activities of the polypeptide having an endonuclease activity of the present invention at temperatures of 0 to 10° C. are about 30 to 70%. On the other hand, the relative activity of Benzonase Nuclease (Novagen) is remarkably dropped to about 0 to 20% at 0 to 10° C. Thus, the polypeptide having an endonuclease activity of the present invention retains a higher endonuclease activity at low temperatures (in particular, 0 to 10° C.) as compared with the commercially available product Benzonase Nuclease.

Inactivation at a lower temperature as compared with bovine pancreatic DNase I is characteristically observed for the polypeptide having an endonuclease activity consists of: the amino acid sequence of SEQ ID NO:3; an amino acid sequence encoded by a nucleic acid containing the nucleotide sequence of SEQ ID NO:4 or a part thereof; or an amino acid sequence in which 1 or more, for example 1 or several, more specifically 1 to 10 amino acid(s) is(are) substituted, deleted, inserted or added in the amino acid sequence of SEQ ID NO:3. For example, bovine pancreatic DNase I retains its activity even at 90° C., whereas the polypeptide having an endonuclease activity of the present invention is completely inactivated by treatment at 70° C. for 30 minutes as described in Example 1.

The polypeptide having an endonuclease activity has the following physical and chemical properties (a) to (h):

(a) substrate specificity: exhibiting its activity on linear double-stranded DNA, circular double-stranded DNA and single-stranded DNA;

(b) completely inactivated by treatment at 70° C. for 30 minutes;

(c) molecular weight: 27 to 31 kDa as determined by SDS-PAGE;

(d) optimal temperature: 30 to 40° C.;

(e) thermostability: retaining its activity at 40° C. for 30 minutes;

(f) optimal pH: 6 to 10;

(g) pH stability: retaining its activity at pH ranging from 4 to 10 upon treatment at 37° C. for 30 minutes; and (h) influence by inhibitor: the activity is inhibited by 5 mM EDTA.

The thermostability can be calculated based on the method as described in Example 1-(5). The polypeptide having an endonuclease activity exhibits high activities at temperatures up to 40° C.; reduction in the activity is observed at temperatures above 40° C.; the activity is rapidly reduced at temperatures above 50° C.; the activity is almost lost at 60° C.; and the polypeptide is completely inactivated at 70° C. This shows that the polypeptide having an endonuclease activity of the present invention is very excellent as a reagent for genetic engineering which is used for elimination of contamination upon PCR or elimination of genome upon RT-PCR.

(2) The Method for Producing a Polypeptide Having an Endonuclease Activity of the Present Invention The polypeptide having an endonuclease activity of the present invention can be produced in large quantities from a culture of a microorganism producing the polypeptide or a transformant having a transferred gene encoding the polypeptide.

Although it is not intended to limit the present invention, for example, a psychrophilic microorganism *Shewanella* sp. strain Ac10 is aerobically cultured at 15° C. Known methods can be used for disrupting the grown cells, extracting and purifying DNA, cleaving the thus obtained DNA with a restriction enzyme and the like. Such methods are described in detail in Sambrook and Russell, Molecular Cloning, A Laboratory Manual 3$^{rd}$ edition, 2001, Cold Spring Harbor Laboratory Press.

The polypeptide having an endonuclease activity of the present invention can be expressed in cells by culturing a transformant transformed with a recombinant plasmid into which a nucleic acid encoding a polypeptide having an endonuclease activity (for example, without limitation, a nucleic acid having the nucleotide sequence of SEQ ID NO:11) or a part thereof is incorporated under appropriate culture conditions (for example, in case of an *Escherichia coli* host, in LB medium (10 g/l Tryptone, 5 g/l yeast extract, 5 g/l NaCl, pH 7.2)). The polypeptide can be obtained from the cultured cells by disrupting the cells and purifying the polypeptide.

In an exemplary method for producing the enzyme or polypeptide using genetic engineering techniques comprises culturing a cell under conditions under which the polypeptide having an endonuclease activity can be expressed, and collecting the polypeptide from the culture. The cell may be a host cell transformed with a vector having an inserted recombinant DNA in which DNA encoding the polypeptide having an endonuclease activity of the present invention is operably linked to an appropriate promoter that functions in the host organism, or a host cell in which such a recombinant DNA is integrated into the host cell DNA. The recombinant DNA may further comprise a regulatory factor such as an operator or a terminator.

The polypeptides having an endonuclease activity of the present invention include ones having the following being further added to the above-mentioned polypeptide of the present invention: a sequence derived from an expression vector such as an expression or translation enhancing sequence (e.g., Perfect DB sequence), or an amino acid sequence such as a tag sequence for purification of an expressed protein (e.g., His tag sequence), Trigger Factor (TF, one of *Escherichia coli* chaperons) tag sequence or a sequence for removing an N-terminal additional sequence of an expressed protein (e.g., Factor Xa sequence, HRV 3 C sequence, Thrombin sequence). Examples of such polypeptides include, but are not limited to, a polypeptide having an endonuclease activity that has the amino acid sequence of SEQ ID NO:8.

There is no specific limitation concerning a vector for producing the polypeptide having an endonuclease activity of the present invention. Any commercially available vector or expression system may be used. For example, the pET system (Novagen) can be used although it is not intended to limit the present invention. In addition, a vector having a promoter that is capable of functioning at low temperatures can be preferably used. Examples thereof include the pCold (cold shock expression) series vectors as described in WO 99/27117.

A method of production using the pCold series vector as described in WO 99/27117 exemplifies one embodiment of the production method of the present invention.

Expression is induced at a low temperature in the cold shock expression system. Then, synthesis of proteins derived from *Escherichia coli* host is suppressed and only the protein of interest can be obtained with high efficiency. Thus, it is expected that the expression level and the solubility are increased as compared with conventional *Escherichia coli* expression systems. Furthermore, a gene of which the expression has been difficult can be expressed as a soluble protein with higher probability due to the solubilization tag function and the chaperon function of Trigger Factor (TF).

Any vector can be preferably used according to the production method of the present invention as long as the vector can be used to express a polypeptide having an endonuclease activity.

Furthermore, a vector that is capable of expressing a polypeptide that is in a form of inclusion body upon expression of the polypeptide, but whose function can be restored by a subsequent refolding procedure may be included, provided that it can be used to obtain the polypeptide having an endonuclease activity.

For example, pCold08-End1 (FERM BP-10313) and pColdTF-End1 which are described in Examples 1 and 2, respectively, can be preferably used as vectors for producing the polypeptide having an endonuclease activity of the present invention. Although it is not intended to limit the present invention, for example, a vector containing the nucleotide sequence of SEQ ID NO:9 can be preferably used.

The polypeptide having an endonuclease activity of the present invention may be produced according to a common procedure for producing a recombinant enzyme. Specifically, after a recombinant microorganism that is capable of producing the polypeptide of the present invention is cultured, the cells can be separated from the culture using a conventional means of separation such as centrifugation or filtration. The cells are disrupted to prepare a cell-free extract, which is used as a crude enzyme solution in the subsequent purification procedure. If the enzyme is secreted outside the cell, a culture supernatant from which the cells have been removed may be used as a crude enzyme solution. Although the crude enzyme solution may be used as it is, it can be used for purification after concentration using a means such as ultrafiltration or precipitation, and/or powderization using an appropriate method, if required. A combination of common means of purifying an enzyme such as chromatography using as an appropriate cation exchange resin, anion exchange resin or hydroxyapatite, affinity chromatography, hydrophobic chromatography, gel filtration and the like can be used for purification.

For example, after a recombinant microorganism that is capable of producing the polypeptide having an endonuclease activity of the present invention is cultured, the cells can be separated from the culture by centrifugation as described in Example 2. The polypeptide having an endonuclease activity of the present invention can be produced by sonicating the cells and subjecting a culture supernatant from which the cells are removed by centrifugation to purification using Q Sepharose Fast Flow (Amersham Biosciences) and Phenyl Sepharose Fast Flow (Amersham Biosciences).

Thus, one can obtain the polypeptide having a function as an endonuclease of the present invention which consists of: the amino acid sequence of SEQ ID NO:10; an amino acid sequence encoded by a nucleic acid containing the nucleotide sequence of SEQ ID NO:11 or a part thereof; or an amino acid sequence in which 1 or more, for example 1 or several, more specifically 1 to 10 amino acid(s) is(are) substituted, deleted, inserted or added in the amino acid sequence of SEQ ID NO:10. The polypeptide utilizes long-chain or short-chain linear double-stranded DNA, circular double-stranded DNA, single-stranded DNA or RNA as a substrate. Its degradation efficiency declines in the following order: long-chain linear double-stranded DNA≈short-chain linear double-stranded DNA>circular double-stranded DNA>single-stranded DNA≈RNA. The endonuclease of the present invention can degrade λ-DNA, pUC119, M13 mp18 single strand DNA as well as 16S and 23S rRNA.

Regarding the polypeptide having an endonuclease activity consists of: the amino acid sequence of SEQ ID NO:3; an amino acid sequence encoded by a nucleic acid containing the nucleotide sequence of SEQ ID NO:4 or a part thereof; or an amino acid sequence in which 1 or more, for example 1 or several, more specifically 1 to 10 amino acid(s) is(are) substituted, deleted, inserted or added in the amino acid sequence of SEQ ID NO:3, the polypeptide utilizes long-chain or short-chain linear double-stranded DNA, circular double-stranded DNA or single-stranded DNA as a substrate. Its degradation efficiency declines in the following order: long-chain linear double-stranded DNA≈short-chain linear double-stranded DNA>circular double-stranded DNA>single-stranded DNA. Since the polypeptide having an endonuclease activity of the present invention degrades λ-DNA, pUC119 and M13 mp18 single strand DNA, it is considered that it does not have specificity for the form (single-stranded or double-stranded) or the nucleotide sequence of the substrate.

(3) The Method for Degrading a Nucleic Acid and the Method for Reducing Viscosity of a Protein Extract Using the Polypeptide Having an Endonuclease Activity of the Present Invention as Well as the Composition and the Kit for the Methods The polypeptide having an endonuclease activity of the present invention as described in (1) above can be preferably used in a method for degrading a nucleic acid. Although it is not intended to limit the present invention, for example, comparison between the polypeptide having an endonuclease activity of the present invention and conventional DNase I for the amount of *Escherichia coli*-derived genome remaining after addition to a supernatant of sonicated *Escherichia coli* and reaction at a low temperature shows that the polypeptide having an endonuclease activity of the present invention can degrade the genomic DNA without influencing the protein of interest.

In particular, one can preferably use according to the method, for degrading a nucleic acid that is as an obstacle to protein purification, a polypeptide having an endonuclease activity that consists of: the amino acid sequence of SEQ ID NO:10; an amino acid sequence encoded by a nucleic acid containing the nucleotide sequence of SEQ ID NO:11 or a part thereof; or an amino acid sequence in which 1 or more, for example 1 or several, more specifically 1 to 10 amino acid(s) is(are) substituted, deleted, inserted or added in the amino acid sequence of SEQ ID NO:10.

The polypeptide having an endonuclease activity of the present invention as described in (1) above can be preferably used in a method for extracting a protein. Although it is not intended to limit the present invention, comparison between the polypeptide having an endonuclease activity of the present invention with conventional DNase I for the viscosity reduction effect upon addition to an extract subjected to protein extraction on ice using a protein extraction reagent kit such as TALON xTractor Buffer Kit (Clontech) shows that the viscosity can be reduced without influencing the protein of interest by the addition of the polypeptide in an amount less by one order of magnitude than DNase I.

In particular, one can preferably use according to the method, for reducing viscosity of an extract which is as an obstacle to protein extraction, a polypeptide having an endonuclease activity that consists of: the amino acid sequence of SEQ ID NO:10; an amino acid sequence encoded by a nucleic acid containing the nucleotide sequence of SEQ ID NO:11 or a part thereof; or an amino acid sequence in which 1 or more, for example 1 or several, more specifically 1 to 10 amino acid(s) is(are) substituted, deleted, inserted or added in the amino acid sequence of SEQ ID NO:10.

The composition or kit of the present invention for elimination of nucleic acids from protein solutions or reduction in viscosity of protein extracts contains the polypeptide having an endonuclease activity of the present invention as described in (1) above. A reaction buffer may be further contained.

The kit is exemplified by a protein extraction reagent kit which additionally contains the polypeptide of the present invention. The protein extraction reagent kit may contain a protease inhibitor, a lytic enzyme and/or a surfactant in addition to the polypeptide having an endonuclease activity of the present invention as described in (1) above and a reaction buffer. For example, PMSF, Lysozyme and Triton X-100 (registered trademark) may be used as the protease inhibitor, the lytic enzyme and the surfactant, respectively.

Furthermore, the polypeptide having an endonuclease activity of the present invention as described in (1) above can be used for elimination of contamination upon PCR or elimination of genome upon RT-PCR.

A composition or a kit containing the polypeptide having an endonuclease activity of the present invention as described in (1) above can be preferably used for the method. A reaction buffer may be further contained.

Although it is not intended to limit the present invention, the kit is exemplified by a kit for PCR which additionally contains the polypeptide having an endonuclease activity of the present invention.

EXAMPLES

The following Examples illustrate the present invention in more detail, but are not to be construed to limit the scope thereof.

Among the procedures described herein, basic procedures including preparation of plasmids and restriction enzyme digestion were carried out as described in Sambrook and Russell, Molecular Cloning, A Laboratory Manual $3^{rd}$ edition, 2001, Cold Spring Harbor Laboratory Press.

Example 1

Examination of Expression of Psychrophilic Microorganism-Derived DNase Using Cold Shock Expression System (1) Construction of Expression Vector An ORF encoding a polypeptide homologous to endonuclease I (GenBank Acc. No. P25736) was deduced from the genomic DNA sequence of a psychrophilic microorganism *Shewanella* sp. strain Ac10.

Synthetic primers 1 and 2 (SEQ ID NOS:1 and 2) were synthesized using a DNA synthesizer based on the sequence of the ORF, and purified according to a conventional method. The synthetic primer 1 is a synthetic DNA that has a nucleotide sequence corresponding to amino acid numbers 1 to 7 in the amino acid sequence of the psychrophilic microorganism-derived DNase (SEQ ID NO:3) and a recognition sequence for a restriction enzyme EcoRI at nucleotide numbers 4 to 9. The synthetic primer 2 is a synthetic DNA that has a nucleotide sequence corresponding to amino acid numbers 247 to 254 in the amino acid sequence of the psychrophilic microorganism-derived DNase (SEQ ID NO:3) and a recognition sequence for a restriction enzyme BamHI at nucleotide numbers 4 to 9.

A PCR was conducted using the synthetic primers. The reaction conditions for the PCR were as follows.

Briefly, a reaction mixture of a total volume of 100 µl was prepared by adding 1 µl of a template DNA (genomic DNA from the psychrophilic microorganism *Shewanella* sp. strain Ac10), 10 µl of 10× Ex Taq Buffer (Takara Bio), 8 µp of dNTP mix (Takara Bio), 100 pmol of the synthetic primer 1, 100 pmol of the synthetic primer 2, 2.5 U of TaKaRa Ex Taq (Takara Bio) and sterile water. The reaction mixture was placed in TaKaRa PCR Thermal Cycler SP (Takara Bio) and subjected to a reaction as follows: 30 cycles of 94° C. for 30 seconds, 58° C. for 30 seconds and 72° C. for 1 minute.

After reaction, 100 µl of the reaction mixture was subjected to electrophoresis on 1.0% agarose gel. The observed about 0.8-kbp DNA fragment of interest was recovered and purified from the electrophoresis gel and subjected to ethanol precipitation. After ethanol precipitation, the recovered DNA was suspended in 5 µl of sterile water, and doubly digested with a restriction enzyme EcoRI (Takara Bio) and a restriction enzyme BamHI (Takara Bio). The EcoRI-BamHI digest was extracted and purified after electrophoresis on 1.0% agarose gel to obtain an EcoRI-BamHI-digested DNA fragment.

Next, pCold08NC2 was constructed based on the description of WO 99/27117 using, as a starting material, a plasmid pMM047.

The vector pCold08NC2 was cleaved with the same restriction enzymes as those used upon preparation of the EcoRI-BamHI-digested DNA fragment, EcoRI and BamHI, and the termini were dephosphorylated. The thus prepared vector and the EcoRI-BamHI-digested DNA fragment were mixed together and ligated to each other using DNA ligation kit (Takara Bio). 10 µl of the ligation mixture was used to transform *Escherichia coli* JM109. Transformants were grown on LB medium containing agar at a concentration of 1.5% (w/v) and ampicillin at a concentration of 100 µg/ml.

A recombinant plasmid was designated as pCold08-End1. This plasmid was designated and indicated as pCold08-End1 and subjected to international deposition at International Patent Organism Depositary, National Institute of Advanced Science and Technology (AIST Tsukuba Central 6, 1-1, Higashi 1-chome, Tsukuba, Ibaraki 305-8566, Japan) under accession number FERM BP-10313 on Feb. 16, 2005 (date of original deposit). The plasmid pCold08-End1 contains a nucleotide sequence (SEQ ID NO:4) encoding amino acid numbers 1 to 254 in the amino acid sequence of the psychrophilic microorganism-derived DNase (SEQ ID NO:3). The protein expressed from the plasmid has a Perfect DB sequence, a His tag sequence, a Factor Xa sequence and a linker at the N terminus of the amino acid sequence. The amino acid sequence of the protein is shown in SEQ ID NO:5. The nucleotide sequence of the nucleic acid encoding the polypeptide is shown in SEQ ID NO:6.

(2) Preparation of Transformant

*Escherichia coli* BL21 was transformed with pCold08-End1 according to a calcium chloride method. A transformant was obtained by screening using LB medium containing agar at a concentration of 1.5% (w/v) and ampicillin at a concentration of 100 µg/ml.

(3) Expression of Psychrophilic Microorganism-Derived DNase

Expression of the psychrophilic microorganism-derived DNase was examined using the transformant obtained in (2) above. *Escherichia coli* BL21 transformed solely with the vector pCold08 without the insert was used as a control. Cultivation was carried out using 5 ml of LB liquid medium (containing 1% Bacto Tryptone, 0.5% yeast extract, 0.5% NaCl, 100 µg/ml ampicillin) at 37° C. When the turbidity (OD600) reached about 0.8, cultivation was carried out at 15° C. for 15 minutes, IPTG was added to the culture at a final concentration of 1 mM and cultivation was further carried out at 15° C. for 24 hours to induce expression. Then, cells were collected and suspended in PBS. The cells were sonicated to prepare a cell extract. Then, a soluble fraction was separated from an insoluble fraction by centrifugation at 15,000×g. Portions of the respective fractions each corresponding to 0.05 OD (OD600) were subjected to SDS-PAGE (5-20% gel). Analysis was carried out by CBB staining and Western blotting using an anti-His Tag antibody.

As a result, expression of the psychrophilic microorganism-derived DNase as a His-Tag fusion protein was observed only for the cell having pCold08-End1 being transferred. The molecular weight of the fusion protein was about 31 kDa as determined by SDS-PAGE. The molecular weight of DNase of the present invention from which the tag sequence had been removed was about 29 kDa.

(4) Measurement of Activity of Psychrophilic Microorganism-Derived DNase

A DNase activity of the soluble fraction of *Escherichia coli* having transferred pCold08-End1 prepared in (3) above was measured. A soluble fraction of sonicated control *Escherichia coli* was also subjected to measurement. The activity was measured as follows.

λ-HindIII digest (Takara Bio) was used as a substrate for the activity measurements. A reaction mixture of a total volume of 50 µl was prepared by adding 1 µg of λ-HindIII digest, the protein sample prepared in (3) above corresponding to 0.025 OD (OD600), 5 µl of 10× reaction buffer (400 mM tris-hydrochloride buffer (pH 7.5), 100 mM sodium chloride, 60 mM magnesium chloride, 10 mM calcium chloride) and nuclease-free water. After the reaction mixture was reacted at 20° C. for 2 hours, 10 μl of the reaction mixture was subjected to electrophoresis on 1% agarose gel for analysis of cleavage product. The results are shown in FIG. 1.

In FIG. 1, the respective lanes represent the following: Lane M: λ-HindIII marker; Lane 1: the soluble fraction of *Escherichia coli* having the vector pCold08 being transferred alone; Lane 2: the soluble fraction of *Escherichia coli* having pCold08-End1 being transferred; Lane 3: the soluble fraction of *Escherichia coli* having the vector pCold08 being transferred alone without the addition of substrate to the reaction system; and Lane 4: the soluble fraction of *Escherichia coli* having pCold08-End1 being transferred without the addition of substrate to the reaction system.

As shown in FIG. 1, the substrate λ-HindIII digest was not degraded with the soluble fraction of *Escherichia coli* having the vector pCold08 being transferred alone (Lane 1), whereas the substrate was degraded with the soluble fraction of *Escherichia coli* having pCold08-End1 being transferred and the activity of the psychrophilic microorganism-derived DNase was observed for the fraction (Lane 2). Comparison between Lanes 2 and 4 revealed that the low-molecular-weight smear band was due to *Escherichia coli*-derived contamination.

(5) Thermostability of Psychrophilic Microorganism-derived DNase

Thermostability was examined using the soluble fraction of *Escherichia coli* having transferred pCold08-End1 prepared in (3) above. The DNase activities were measured after allowing to stand for 30 minutes in PBS at various temperatures (4° C. to 90° C.). Bovine pancreas DNase I (Takara Bio) was used as a control. λ-HindIII digest was used as a substrate for the activity measurements. A reaction mixture of a total volume of 50 μl was prepared by adding 1 μg of λ-HindIII digest, the soluble fraction of *Escherichia coli* having transferred pCold08-End1 prepared in (3) above corresponding to 0.02 OD (OD600) or 8 U of bovine pancreas DNase I, 5 μl of 10× reaction buffer (400 mM tris-hydrochloride buffer (pH 7.5), 100 mM sodium chloride, 60 mM magnesium chloride, 10 mM calcium chloride) and nuclease-free water. After the reaction mixture was reacted at 20° C. (or 37° C. in cases of bovine pancreas DNase I) for 30 minutes, 10 μl of the reaction mixture was subjected to electrophoresis on 1% agarose gel for analysis of cleavage product. The results are shown in FIG. 2.

Figure 2:
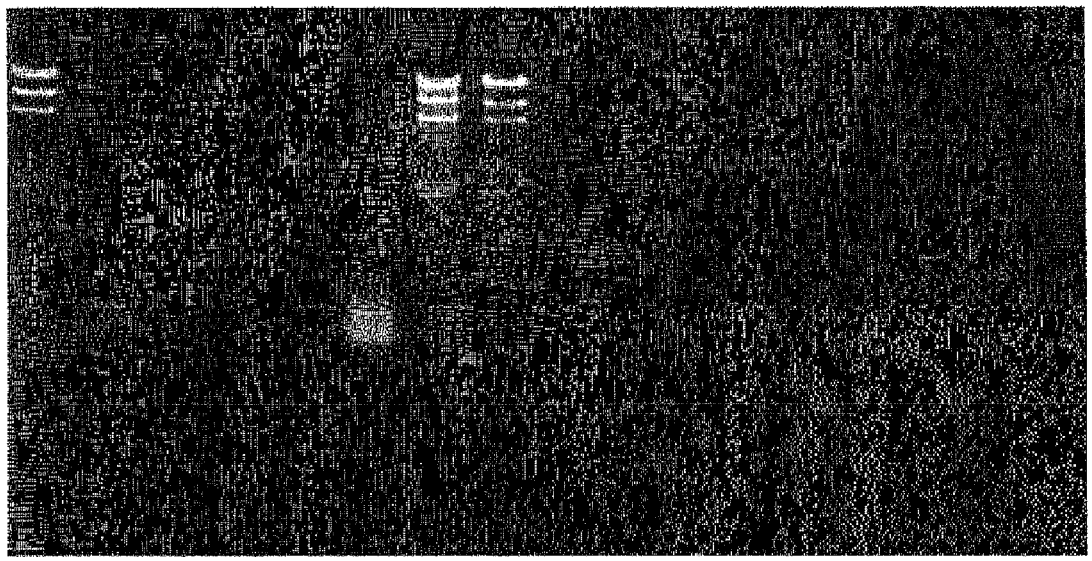
FIG. 2 illustrates results of thermostability test for a psychrophilic microorganism-derived DNase.

In FIG. 2, the respective lanes represent the following: Lane M: λ-HindIII marker; Lanes 1-8: the psychrophilic microorganism-derived DNase of the present invention; and Lanes 9-16: bovine pancreas DNase I.

Furthermore, the respective lanes in FIG. 2 represent ones allowed to stand for 30 minutes at the temperatures indicated below: Lanes 1 and 9: 4° C.; Lane 2: 10° C.; Lane 3: 20° C.; Lanes 4 and 10: 30° C.; Lanes 5 and 11: 40° C.; Lanes 6 and 12: 50° C.; Lanes 7 and 13: 60° C.; Lanes 8 and 14: 70° C.; Lane 15: 80° C.; and Lane 16: 90° C.

As shown in FIG. 2, the psychrophilic microorganism-derived DNase exhibited high activities at temperatures ranging from 4° C. (Lane 1) to 40° C. (Lane 5); inactivation was observed at 50° C. (Lane 6); the DNase was almost inactivated at 60° C. (Lane 7); and complete inactivation was observed at 70° C. (Lane 8). On the other hand, bovine pancreas DNase I retained its activity even at 90° C. (Lane 16).

(6) Optimal Temperature of Psychrophilic Microorganism-derived DNase

Optimal temperature was examined using the soluble fraction of *Escherichia coli* having transferred pCold08-End1 prepared in (3) above. Bovine pancreas DNase I (Takara Bio) was used as a control. λ-HindIII digest was used as a substrate for the activity measurements. A reaction mixture of a total volume of 50 μl was prepared by adding 1 μg of λ-HindIII digest, the soluble fraction of *Escherichia coli* having transferred pCold08End1 prepared in (3) above corresponding to $5 \times 10^{-4}$ or $5 \times 10^{-5}$ OD (OD600) (or 0.1 mU or 1 mU of bovine pancreas DNase I), 5 μl of 10× reaction buffer (400 mM tris-hydrochloride buffer (pH 7.5), 100 mM sodium chloride, 60 mM magnesium chloride, 10 mM calcium chloride) and nuclease-free water. After the reaction mixture was reacted at a temperature within a range of 10 to 70° C. for 30 minutes, 10 μl of the reaction mixture was subjected to electrophoresis on 1% agarose gel for analysis of cleavage product. The results are shown in FIG. 3.

Figure 3:
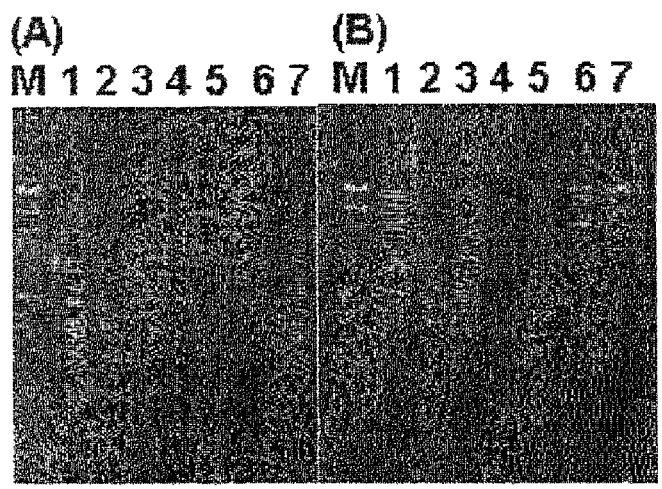
FIG. 3 illustrates results of optimal temperature test for a psychrophilic microorganism-derived DNase.
Figure 3:
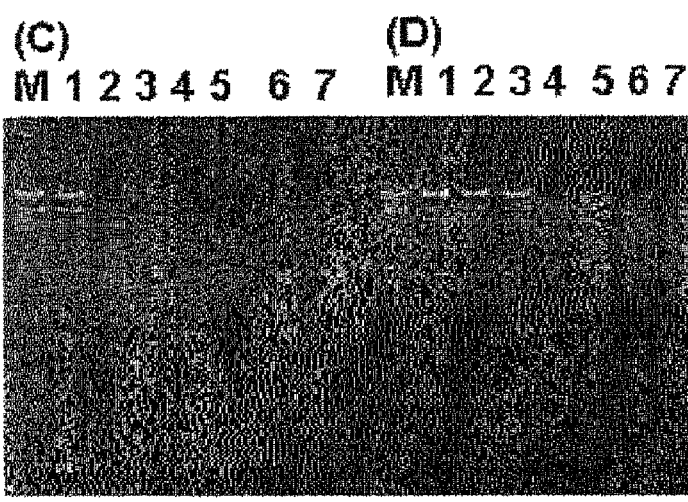

In FIG. 3, the respective panels represent the following: (A): the psychrophilic microorganism-derived DNase of the present invention corresponding to $5 \times 10^{-4}$ OD; (B): the psychrophilic microorganism-derived DNase of the present invention corresponding to $5 \times 10^{-5}$ OD; (C): 1 mU of bovine pancreas DNase I; and (D): 0.1 mU of bovine pancreas DNase I. In all panels, the respective lanes represent the following: Lane M: λ-HindIII marker; Lanes 1-7: ones allowed to stand for 30 minutes at the temperatures indicated below: Lane 1: 10° C.; Lane 2: 20° C.; Lane 3: 30° C.; Lane 4: 40° C.; Lane 5: 50° C.; Lane 6: 60° C.; and Lane 7: 70° C.

As shown in FIG. 3, the psychrophilic microorganism-derived DNase exhibited high activities at low-to-normal temperatures (10-40° C.) with the optimal temperature being about 30-40° C. On the other hand, bovine pancreas DNase I exhibited low activities at low temperatures and higher activities were observed at higher temperatures.

(7) Substrate Specificity of Psychrophilic Microorganism-derived DNase

Activities on various substrates were measured using the soluble fraction of *Escherichia coli* having transferred pCold08-End1 prepared in (3) above. In addition to λ-HindIII digest, λ DNA (Takara Bio), pUC119 (Takara Bio) and M13 mp18 Single Strand DNA (Takara Bio) were used as substrates for the examination. A reaction mixture of a total volume of 50 μl was prepared by adding 1 μg of the substrate, the soluble fraction of *Escherichia coli* having transferred pCold08-End1 prepared in (3) above corresponding to $5 \times 10^{-3}$, $5 \times 10^{-4}$, $5 \times 10^{-5}$ or $5 \times 10^{-6}$ OD (OD600), 5 μl of 10× reaction buffer (400 mM tris-hydrochloride buffer (pH 7.5), 100 mM sodium chloride, 60 mM magnesium chloride, 10 mM calcium chloride) and nuclease-free water. After the reaction mixture was reacted at 37° C. for 30 minutes, 10 μl of the reaction mixture was subjected to electrophoresis on 1% agarose gel for analysis of cleavage product. The results are shown in FIG. 4.

Figure 4:
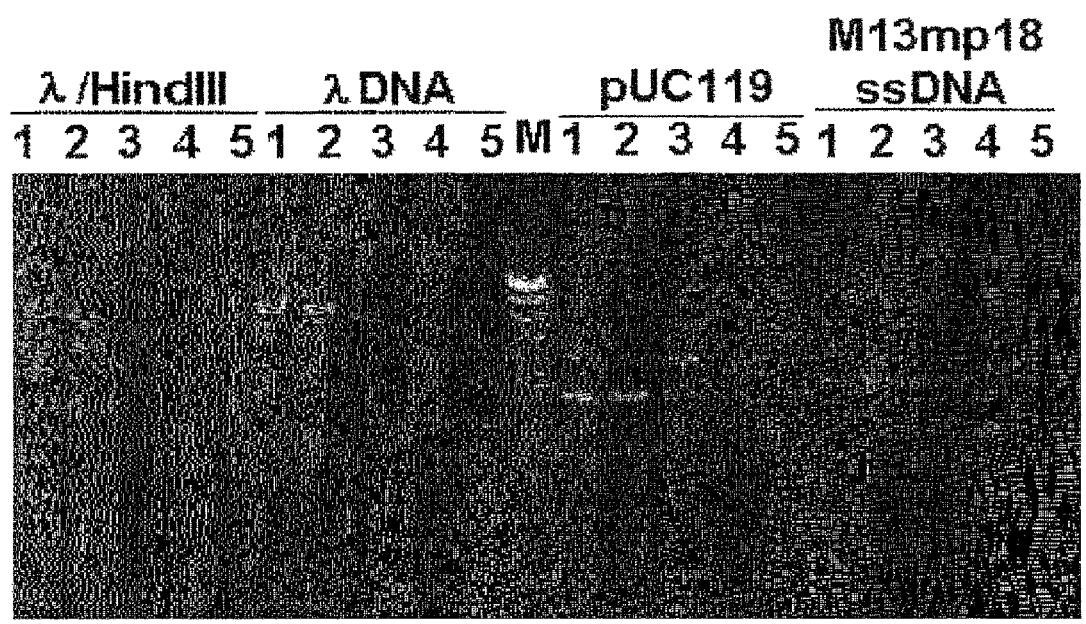
FIG. 4 illustrates results of substrate specificity test for a psychrophilic microorganism-derived DNase.

In FIG. 4, the respective lanes represent the following: Lane M: λ-HindIII marker; Lane 1: without the addition of enzyme; Lanes 2-5: with the psychrophilic microorganism-derived DNase of the present invention corresponding to the amounts indicated below; Lane 2: $5 \times 10^{-6}$ OD; Lane 3: $5 \times 10^{-5}$ OD; Lane 4: $5 \times 10^{-4}$ OD; and Lane 5: $5 \times 10^{-3}$ OD.

As shown in FIG. 4, all the substrates including linear double-stranded DNA (λ DNA, 48.5 kbp), circular double-stranded DNA (pUC119, 3.2 kbp) and single-stranded DNA (M13 mp18 Single Strand DNA, 7.2 kbp) were degraded. The substrate degradation efficiency with the endonuclease of the present invention declined in the following order: long-chain linear double-stranded DNA≈short-chain linear double-stranded DNA>circular double-stranded DNA>single-stranded DNA. Since the endonuclease of the present invention degraded λ-DNA, pUC119 and M13 mp18 single strand DNA, it is considered that it does not have specificity for the form (single-stranded or double-stranded) or the nucleotide sequence of the substrate.

(8) Influence of EDTA on Reaction with Psychrophilic Microorganism-derived DNase Influence of EDTA on reaction was examined using the soluble fraction of *Escherichia coli* having transferred pCold08-End1 prepared in (3) above. DNase activities were measured in the presence of EDTA at varying concentrations (0, 0.2, 1, 5 mM) in reaction mixtures. Bovine pancreas DNase I was used as a control. λ-HindIII digest was used as a substrate for the activity measurements. A reaction mixture of a total volume of 50 μl was prepared by adding 1 μg of λ-HindIII digest, the soluble fraction of *Escherichia coli* having transferred pCold08-End1 prepared in (3) above corresponding to $5\times10^{-4}$ OD (OD600) or 1 mU of bovine pancreas DNase I, 5 μl of 10× reaction buffer (400 mM tris-hydrochloride buffer (pH 7.5), 100 mM sodium chloride, 60 mM magnesium chloride, 10 mM calcium chloride) and nuclease-free water. After the reaction mixture was reacted at 37° C. for 30 minutes, 10 μl of the reaction mixture was subjected to electrophoresis on 1% agarose gel for analysis of cleavage product. The results are shown in FIG. 5.

Figure 5:
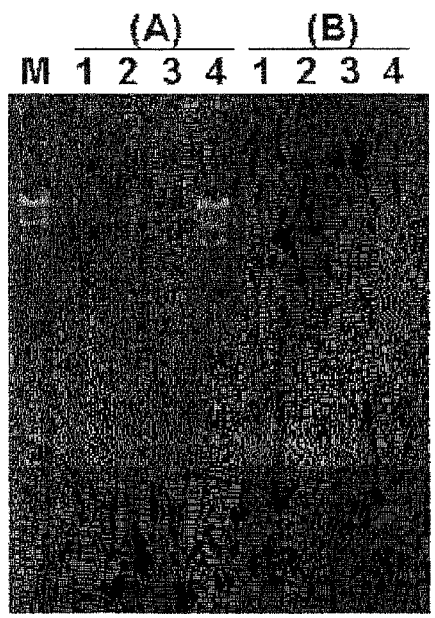
FIG. 5 illustrates results of test for influence of EDTA on reaction with a psychrophilic microorganism-derived DNase.

In FIG. 5, the respective panels represent the following: (A): the psychrophilic microorganism-derived DNase of the present invention; and (B): bovine pancreas DNase I. In both panels, the respective lanes represent the following: Lane M: λ-HindIII marker; Lanes 1-4: with the addition of EDTA to the reaction system at the concentrations indicated below; Lane 1: 0 mM; Lane 2: 0.2 mM; Lane 3: 1 mM; and Lane 4: 5 mM.

As shown in FIG. 5, the psychrophilic microorganism-derived DNase exhibited no activity in the presence of 5 mM EDTA (Panel (A), Lane 4), whereas bovine pancreas DNase I retained its activity (Panel (B), Lane 4).

(9) Optimal pH of Psychrophilic Microorganism-derived DNase

Optimal pH was examined using the soluble fraction of *Escherichia coli* having transferred pCold08-End1 prepared in (3) above.

λ-HindIII digest was used as a substrate for the activity measurements. Examination was carried out using the following buffers: pH 4 and 5: sodium acetate buffer; pH 6, 7 and 8: sodium phosphate buffer; pH 7.5: tris-hydrochloride buffer; pH 9 and 10: sodium borate buffer.

A reaction mixture of a total volume of 50 μl was prepared by adding 1 μg of λ-HindIII digest, the soluble fraction of *Escherichia coli* having transferred pCold08-End1 prepared in (3) above corresponding to $5\times10^{-4}$ or $5\times10^{-5}$ OD (OD600), 5 μl of 10× reaction buffer (400 mM of the above-mentioned buffer, 100 mM sodium chloride, 60 mM magnesium chloride, 10 mM calcium chloride) and nuclease-free water. After the reaction mixture was reacted at 37° C. for 30 minutes at varying pH (pH 4-10), 10 μl of the reaction mixture was subjected to electrophoresis on 1% agarose gel for analysis of cleavage product. The results are shown in FIG. 6.

Figure 6:
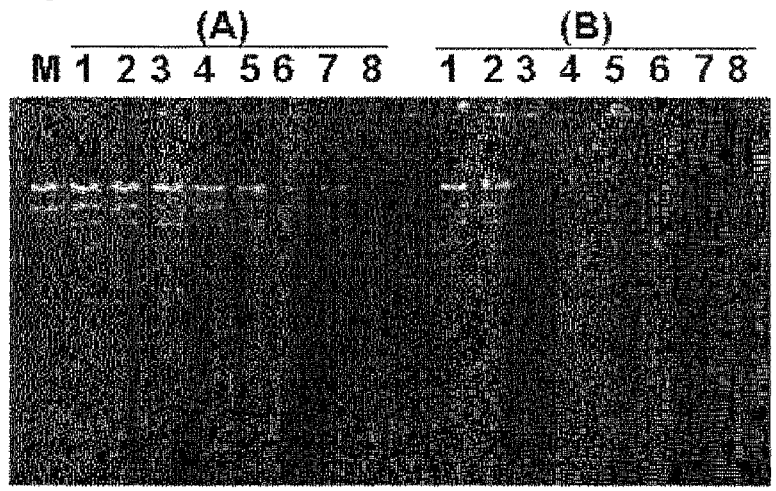
FIG. 6 illustrates results of optimal pH test for a psychrophilic microorganism-derived DNase.

In FIG. 6, the respective panels represent the following: (A) $5\times10^{-5}$ OD; and (B) $5\times10^{-4}$ OD. In both panels, the respective lanes represent the following: Lane M: λ-HindIII marker; Lane 1: pH 4; Lane 2: pH 5; Lane 3: pH 6; Lane 4: pH 7; Lane 5: pH 7.5; Lane 6: pH 8; Lane 7: pH 9; and Lane 8: pH 10.

As a result, cleavage of the substrate was observed in Lanes 3-8 of Panel (B). Thus, the optimal pH of the psychrophilic microorganism-derived DNase was pH 6-10.

(10) pH Stability of Psychrophilic Microorganism-derived DNase pH stability was examined using the soluble fraction of *Escherichia coli* having transferred pCold08-End1 prepared in (3) above.

DNase activities were measured after allowing to stand in various buffers each at a concentration of 40 mM (pH 4 and 5: sodium acetate buffer; pH 6, 7 and 8: sodium phosphate buffer; pH 7.5: tris-hydrochloride buffer; pH 9 and 10: sodium borate buffer) at 37° C. for 30 minutes. λ-HindIII digest was used as a substrate for the activity measurements. A reaction mixture of a total volume of 50 μl was prepared by adding 1 μg of λ-HindIII digest, the sample that had been allowed to stand in one of the various buffers at 37° C. for 30 minutes corresponding to $5\times10^{-4}$ OD (OD600), 5 μl of 10× reaction buffer (400 mM tris-hydrochloride buffer (pH 7.5), 100 mM sodium chloride, 60 mM magnesium chloride, 10 mM calcium chloride) and nuclease-free water. After the reaction mixture was reacted at 37° C. for 30 minutes, 10 μl of the reaction mixture was subjected to electrophoresis on 1% agarose gel for analysis of cleavage product. The results are shown in FIG. 7.

Figure 7:
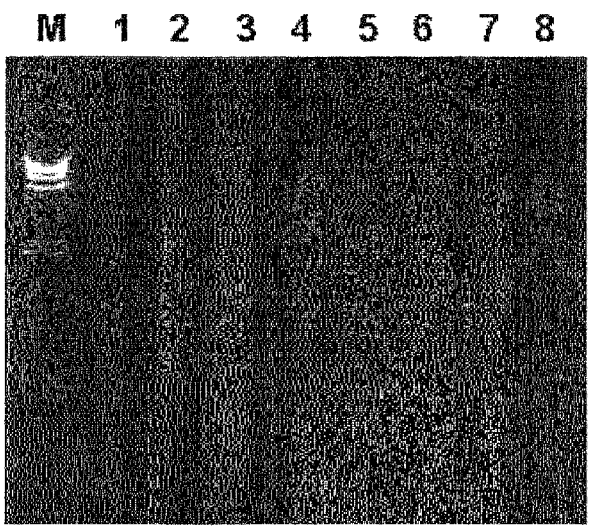
FIG. 7 illustrates results of pH stability test for a psychrophilic microorganism-derived DNase.

In FIG. 7, the respective lanes represent the following: Lane M: λ-HindIII marker; Lane 1: pH 4; Lane 2: pH 5; Lane 3: pH 6; Lane 4: pH 7; Lane 5: pH 7.5; Lane 6: pH 8; Lane 7: pH 9; and Lane 8: pH 10.

As a result, cleavage of the substrate was observed in Lanes 1-8. Thus, the psychrophilic microorganism-derived DNase retained its activity at pH 4-10.

Example 2

Examination of Expression of Psychrophilic Microorganism-derived Endonuclease Using Cold Shock Expression System (1) Construction of Expression Vector Construction of an expression system that is more suitable for industrial scale production than the expression system of the recombinant plasmid pCold08-End1 constructed in Example 1 above was examined.

In addition to the synthetic primer 2 synthesized in Example 1(1) above, a synthetic primer 3 (SEQ ID NO:7) was synthesized using a DNA synthesizer and purified according to a conventional method. The synthetic primer 3 is a synthetic DNA that has a nucleotide sequence corresponding to amino acid numbers 1 to 7 in the amino acid sequence of the psychrophilic microorganism-derived DNase (SEQ ID NO:3) and a recognition sequence for a restriction enzyme NdeI at nucleotide numbers 4 to 9.

A PCR was conducted using the synthetic primers. The reaction conditions for the PCR were as follows.

Briefly, a reaction mixture of a total volume of 100 μl was prepared by adding 1 μl of a template DNA (pCold08-End1), 10 μl of 10× Ex Taq Buffer (Takara Bio), 8 μl of dNTP mix (Takara Bio), 100 pmol of the synthetic primer 2, 100 pmol of the synthetic primer 3, 2.5 U of TaKaRa Ex Taq (Takara Bio) and sterile water. The reaction mixture was placed in TaKaRa PCR Thermal Cycler SP (Takara Bio) and subjected to a reaction as follows: 30 cycles of 94° C. for 30 seconds, 58° C. for 30 seconds and 72° C. for 1 minute.

After reaction, 100 μl of the reaction mixture was subjected to electrophoresis on 1.0% agarose gel. The observed about 0.8-kbp DNA fragment of interest was recovered and purified from the electrophoresis gel and subjected to ethanol precipitation. After ethanol precipitation, the recovered DNA was suspended in 5 μl of sterile water, and doubly digested with a restriction enzyme NdeI (Takara Bio) and a restriction enzyme BamHI (Takara Bio) The NdeI-BamHI digest was extracted and purified after electrophoresis on 1.0% agarose gel to obtain a NdeI-BamHI-digested DNA fragment.

Next, the vector pColdTF (Takara Bio) was cleaved with the same restriction enzymes as those used upon preparation of the NdeI-BamHI-digested DNA fragment, NdeI and BamHI, and the termini were dephosphorylated. The thus prepared vector and the NdeI-BamHI-digested DNA fragment were mixed together and ligated to each other using DNA ligation kit (Takara Bio). 10 µl of the ligation mixture was used to transform *Escherichia coli* JM109. Transformants were grown on LB medium containing agar at a concentration of 1.5% (w/v) and ampicillin at a concentration of 100 µg/ml.

A recombinant plasmid was designated as pColdTF-End1. The plasmid pColdTF-End1 contains a nucleotide sequence (SEQ ID NO:4) encoding amino acid numbers 1 to 254 in the amino acid sequence of the psychrophilic microorganism-derived DNase (SEQ ID NO:3). The protein expressed from the plasmid has a Perfect DB sequence, a His tag sequence, a TF tag sequence, a HRV 3C sequence, a Thrombin sequence, a Factor Xa sequence and a linker at the N terminus of the amino acid sequence. The amino acid sequence of the protein is shown in SEQ ID NO:8. The nucleotide sequence of the nucleic acid encoding the polypeptide is shown in SEQ ID NO:9.

(2) Preparation of Transformant

*Escherichia coli* BL21 was transformed with pColdTF-End1 according to a calcium chloride method. A transformant was obtained by screening using LB medium containing agar at a concentration of 1.5% (w/v) and ampicillin at a concentration of 100 µg/ml.

(3) Expression of Psychrophilic Microorganism-derived Endonuclease

Expression of the psychrophilic microorganism-derived endonuclease was examined using the transformant obtained in (2) above. *Escherichia coli* BL21 transformed solely with the vector pColdTF without the insert was used as a control. Cultivation was carried out using 5 ml of LB liquid medium (containing 1% Bacto Tryptone, 0.5% yeast extract, 1% NaCl, 100 µg/ml ampicillin) at 37° C. When the turbidity (OD600) reached about 0.8, cultivation was carried out at 15° C. for 15 minutes, IPTG was added to the culture at a final concentration of 1 mM and cultivation was further carried out at 15° C. for 24 hours to induce expression. Then, cells were collected and suspended in PBS. The cells were sonicated to prepare a cell extract. Then, a soluble fraction was separated from an insoluble fraction by centrifugation at 15,000×g.

(4) Measurement of Endonuclease Activity Using Soluble Fraction of *Escherichia coli* Having Transferred pColdTF-End1

An endonuclease activity was measured using the soluble fraction of *Escherichia coli* having transferred pColdTF-End1 prepared in (3) above. A control was prepared in a similar manner from *Escherichia coli* having the vector pColdTF being transferred alone. The activity was measured as follows.

λ-HindIII digest (Takara Bio) was used as a substrate for the activity measurements. A reaction mixture of a total volume of 50 µl was prepared by adding 1 µg of λ-HindIII digest, the soluble fraction of *Escherichia coli* having transferred pColdTF-End1 corresponding to 0.00625 OD (OD600), 5 µl of 10× reaction buffer (400 mM tris-hydrochloride buffer (pH 7.5), 100 mM sodium chloride, 60 mM magnesium chloride, 10 mM calcium chloride) and nuclease-free water. After the reaction mixture was reacted at 37° C. for 30 minutes, 10 µl of the reaction mixture was subjected to electrophoresis on 1% agarose gel for analysis of cleavage product. The results are shown in FIG. 8.

Figure 8:
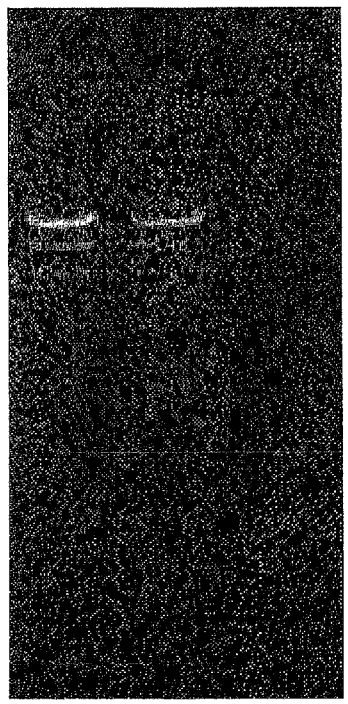
FIG. 8 illustrates results of activity measurement test for the endonuclease of the present invention.

In FIG. 8, the respective lanes represent the following: Lane 1: without the addition of soluble fraction; Lane 2: the soluble fraction of *Escherichia coli* having the vector pColdTF being transferred alone; and Lane 3: the soluble fraction of *Escherichia coli* having pColdTF-End1 being transferred.

As shown in FIG. 8, the substrate λ-HindIII digest was not degraded without the addition of a soluble fraction or with the soluble fraction of *Escherichia coli* having the vector pColdTF being transferred alone (Lanes 1 and 2), whereas the substrate was degraded with the soluble fraction of *Escherichia coli* having pColdTF-End1 being transferred (Lane 3) and the activity of the psychrophilic microorganism-derived endonuclease of the present invention was observed.

(5) Expression, Purification and Activity Measurement of Psychrophilic Microorganism-derived Endonuclease The transformant obtained in (2) above was used for expression, purification and activity measurement of the psychrophilic microorganism-derived endonuclease. Cultivation was carried out using two vessels each containing 100 ml of LB liquid medium (containing 1% Bacto Tryptone, 0.5% yeast extract, 1% NaCl, 100 µg/ml ampicillin) at 37° C. until the turbidity (OD600) reached about 0.6. The culture was inoculated into 20 L of LB liquid medium. When the turbidity (OD600) reached about 0.6, cultivation was carried out at 15° C. for 15 minutes, IPTG was added to the culture at a final concentration of 1 mM and cultivation was further carried out at 15° C. for 24 hours to induce expression. Then, 36.4 g of wet cells were collected and suspended in 360 ml of 10 mM tris-hydrochloride buffer (pH 7.5) and 1 mM PMSF. The cells were sonicated, and 370 ml of a soluble fraction was obtained by centrifugation at 18,000×g for 20 minutes.

Purification was carried out using 370 ml of the soluble fraction as follows.

Briefly, Q Sepharose Fast Flow (Amersham Biosciences) corresponding to a resin volume of 100 ml was filled into a φ 35-mm column and equilibrated with 500 ml of 10 mM tris-hydrochloride buffer (pH 7.5) and 1 mM PMSF. Then, 370 ml of the soluble fraction was applied thereto. The resin was washed successively with 300 ml of the same buffer and the buffer containing 300 mM sodium chloride. Elution was carried out using 300 ml of the buffer containing 1 M sodium chloride. Ammonium sulfate at a final concentration of 2 M was added to the eluted fraction which contained the endonuclease activity, and 330 ml of a supernatant was obtained by centrifugation at 18,000 g for 20 minutes. The thus obtained supernatant was applied to Phenyl Sepharose Fast Flow (Amersham Biosciences) corresponding to a resin volume of 30 ml in a φ 16-mm column equilibrated with 300 ml of 10 mM tris-hydrochloride buffer (pH 7.5) and 2 M ammonium sulfate. Unnecessary proteins other than the protein of interest were removed by washing with 225 ml of the same buffer. After washing, elution was carried out using a gradient from 10 mM tris-hydrochloride buffer (pH 7.5) and 2 M ammonium sulfate to 10 mM tris-hydrochloride buffer (pH 7.5) and 0 M ammonium sulfate (10 ml/fr., a total of 600 ml). Endonuclease activities were measured for the respective fractions and fr. 28-36 for which activities were observed were collected as a pool of 90 ml. The pool was dialyzed twice against 5 L of 10 mM tris-hydrochloride buffer (pH 7.5), and the dialysate was concentrated using Vivaspin (Vivascience) to obtain 5.5 ml of a protein sample.

A portion of the concentrate was subjected to 5-20% SDS-polyacrylamide gel electrophoresis to determine molecular weights of proteins in a protein sample obtained by dialyzing and concentrating the fractions fr. 28-36 for which activities were observed. The results are shown in FIG. 9.

Figure 9:
FIG. 9 illustrates results of SDS-polyacrylamide gel electrophoresis test for determining the molecular weight of the endonuclease of the present invention.

In FIG. 9, the respective lanes represent the following: Lane M: molecular weight marker 97, 66, 45, 31, 21, 14 KDa; and Lane 1: the protein sample obtained by dialyzing and concentrating the fractions fr. 28-36 for which activities were observed.

As a result, a main protein band was observed at a position corresponding to a molecular weight of about 25 KDa. 10 residues of the N-terminal amino acid sequence were analyzed for the protein band of about 25 KDa. Since the sequence was identical to the amino acid sequence of amino acid numbers 36 to 45 in SEQ ID NO:3, it was found that the tag sequence and a portion at the N terminus of the protein of interest had been deleted in the active protein. The amino acid sequence of the active protein was determined based on the average molecular weight measured according to the MALDI-TOF MS measurement method. The amino acid sequence of the active protein and the nucleotide sequence encoding the polypeptide are shown in SEQ ID NOS:10 and 11, respectively.

The active protein was used in activity determination below.

Salmon testis DNA (Wako Pure Chemical Industries) was used as a substrate for quantitative activity measurements. 100 µl of the protein sample prepared as described above was added to 500 µl of a substrate solution (40 µg/ml; 100 mM tris-hydrochloride buffer (pH 7.5) and 5 mM magnesium chloride) to prepare a reaction mixture. An amount of an enzyme that increases absorbance at 260 nm by 0.001 in 1 minute at 37° C. was defined as 1 U. The total activity of the obtained endonuclease was 790,000 U.

Example 3

Examination of Properties of Psychrophilic Microorganism-derived Endonuclease (1) Reactivity of Psychrophilic Microorganism-derived Endonuclease at Low Temperatures The endonuclease activity was examined at low temperatures using the polypeptide having an endonuclease activity prepared in Example 2(5) above. Benzonase (registered trademark) Nuclease from Novagen was used as a control, and salmon testis DNA (Wako Pure Chemical Industries) was used as a substrate for activity measurements. 100 µl of a solution containing the polypeptide having an endonuclease activity prepared in Example 2(5) above (2.3 U; 10 mM tris-hydrochloride buffer (pH 7.5) and 10 mM magnesium chloride) was added to 500 µl of the substrate solution (40 µg/ml; 100 mM tris-hydrochloride buffer (pH 7.5) and 5 mM magnesium chloride) to prepare a reaction mixture. Activities were determined by measuring increases in absorbance at 260 nm after reacting for 10 minutes at temperatures of 0, 5, 10, 15 and 20° C. Activities were also measured using Benzonase in a similar manner in a reaction mixture having the same composition as the above. The results are shown in FIG. 10.

Figure 10:
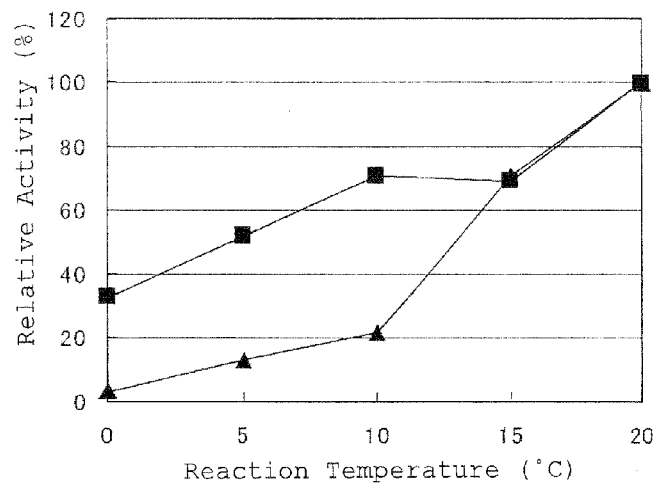
FIG. 10 illustrates results of comparative test for reactivity at low temperatures between the endonuclease of the present invention and Benzonase.

In FIG. 10, squares (■) represent results for the polypeptide having an endonuclease activity prepared in Example 2(5) above and triangles (▲) represent results for Benzonase.

Relative activities (%) were calculated and compared defining the activity at 20° C. as 100. As shown in FIG. 10, the relative activities of the polypeptide having an endonuclease activity of the present invention at 0 to 10° C. were about 30 to 70%, whereas the relative activities of Benzonase Nuclease at 0 to 10° C. were remarkably dropped to about 0 to 20%.

Thus, the polypeptide having an endonuclease activity of the present invention retained a higher endonuclease activity at low temperatures (particularly at 0 to 10° C.) as compared with the commercially available product Benzonase Nuclease.

(2) Substrate Specificity of Psychrophilic Microorganism-derived Endonuclease

Activities on various substrates were measured using the polypeptide having an endonuclease activity prepared in Example 2(5) above. In addition to λ-HindIII digest, λ DNA (Takara Bio), pUC119 (Takara Bio), M13 mp18 Single Strand DNA (Takara Bio) as well as 16S and 23S rRNA (Roche) were used as substrates for the examination. A reaction mixture of a total volume of 50 µl was prepared by adding 1 µg of the substrate, 1 U, 0.1 U, 0.01 U or 0.001 U of the polypeptide having an endonuclease activity prepared in Example 2(5) above, 5 µl of 10× reaction buffer (400 mM tris-hydrochloride buffer (pH 7.5), 100 mM sodium chloride, 60 mM magnesium chloride, 10 mM calcium chloride) and nuclease-free water. After the reaction mixture was reacted at 37° C. for 30 minutes, 10 µl of the reaction mixture was subjected to electrophoresis on 1% agarose gel for analysis of cleavage product. The results are shown in FIG. 11.

Figure 11:
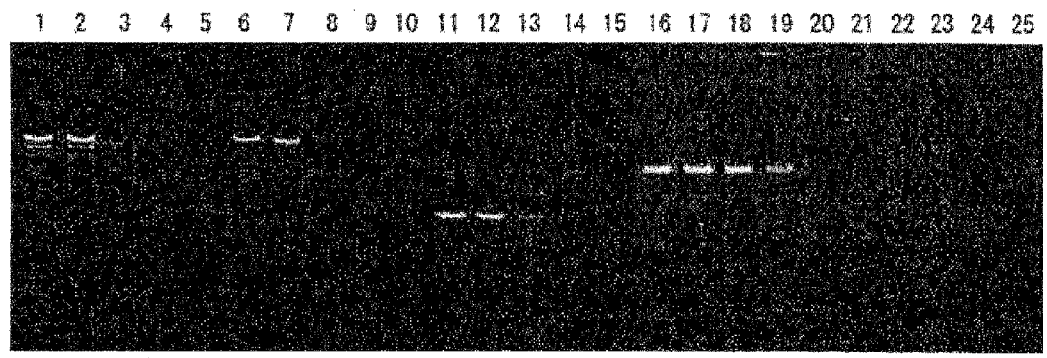
FIG. 11 illustrates results of substrate specificity test for the endonuclease of the present invention.

In FIG. 11, the respective lanes represent the following: Lanes 1-5.: λ-HindIII digest as a substrate; Lanes 6-10: λ DNA as a substrate; Lanes 11-15: pUC119 as a substrate; Lanes 16-20: M13 mp18 Single Strand DNA as a substrate; Lanes 21-25: 16S and 23S rRNA as a substrate; Lanes 1, 6, 11, 16 and 21: without the addition of enzyme; Lanes 2, 7, 12, 17 and 22: 0.001 U of the psychrophilic microorganism-derived endonuclease of the present invention; Lanes 3, 8, 13, 18 and 23: 0.01 U of the psychrophilic microorganism-derived endonuclease of the present invention; Lanes 4, 9, 14, 19 and 24: 0.1 U of the psychrophilic microorganism-derived endonuclease of the present invention; and Lanes 5, 10, 15, 20 and 25: 1 U of the psychrophilic microorganism-derived endonuclease of the present invention.

As shown in FIG. 11, it was confirmed that the endonuclease of the present invention degrades all the substrates including linear double-stranded DNA (λ DNA, 48.5 kbp), circular double-stranded DNA (pUC119, 3.2 kbp), single-stranded DNA (M13 mp18 Single Strand DNA, 7.2 kbp) and RNA (16S and 23S rRNA). The substrate degradation efficiency with the endonuclease of the present invention declined in the following order: long-chain linear double-stranded DNA≈short-chain linear double-stranded DNA>circular double-stranded DNA>single-stranded DNA≈RNA.

(3) Optimal pH of Psychrophilic Microorganism-derived Endonuclease

Optimal pH was examined using the soluble fraction of *Escherichia coli* having transferred pColdTF-End1 prepared in Example 2(3) above.

λ-HindIII digest was used as a substrate for the activity measurements. Examination was carried out using the following buffers: pH 4 and 5: sodium acetate buffer; pH 6 and 7: sodium phosphate buffer; pH 7.5 and 8: tris-hydrochloride buffer; pH 9 and 10: sodium borate buffer.

A reaction mixture of a total volume of 50 µl was prepared by adding 1 µg of λ-HindIII digest, the soluble fraction of *Escherichia coli* having transferred pColdTF-End1 prepared in Example 2(3) above corresponding to $7 \times 10^{-4}$ OD (OD600), 5 µl of 10× reaction buffer (400 mM of the above-mentioned buffer, 100 mM sodium chloride, 1 M magnesium chloride, 10 mM calcium chloride) and nuclease-free water. After the reaction mixture was reacted at 37° C. for 30 minutes at varying pH (pH 4-10), 10 µl of the reaction mixture was subjected to electrophoresis on 1% agarose gel for analysis of cleavage product. The results are shown in FIG. 12.

Figure 12:
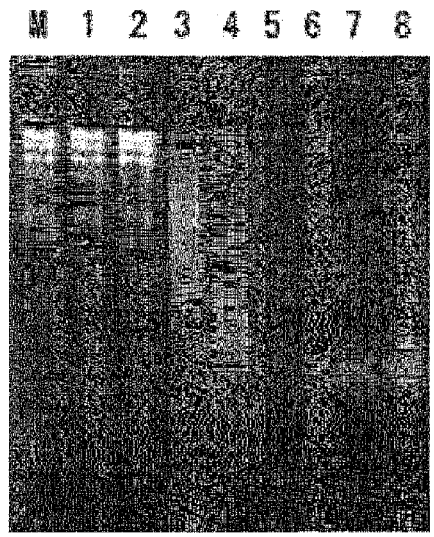
FIG. 12 illustrates results of optimal pH test for the endonuclease of the present invention.

In FIG. 12, the respective lanes represent the following: Lane M: λ-HindIII marker; Lane 1: pH 4; Lane 2: pH 5; Lane 3: pH 6; Lane 4: pH 7; Lane 5: pH 7.5; Lane 6: pH 8; Lane 7: pH 9; and Lane 8: pH 10.

As a result, cleavage of the substrate was observed in Lanes 3-8. Thus, the optimal pH of the polypeptide having an endonuclease activity of the present invention was pH 6-10.

(4) Influence of Various Additives on Psychrophilic Microorganism-derived Endonuclease Influence of various additives was examined using the polypeptide having an endonuclease activity prepared in Example 2(5) above. Salmon testis DNA (Wako Pure Chemical Industries) was used as a substrate for activity measurements. 100 μl of a solution containing 0.25 U of the polypeptide having an endonuclease activity prepared in Example 2(5) above was added to 500 μl of a substrate solution (40 μg/ml; 100 mM tris-hydrochloride buffer (pH 7.5) and 100 mM magnesium chloride (eliminated when influence of magnesium ion was examined)) to prepare a reaction mixture. Increases in absorbance at 260 nm at 37° C. were determined to examine influence of various additives.

1. Influence of Magnesium Ion

Influence of magnesium ion concentration was examined by adding magnesium chloride at a final concentration of 0, 0.8, 1.7, 4.2, 5, 10, 20, 40, 80, 100, 120, 140 or 160 mM to a reaction mixture having the above-mentioned composition. The results are shown in FIG. 13-1.

Figures 1, 13:
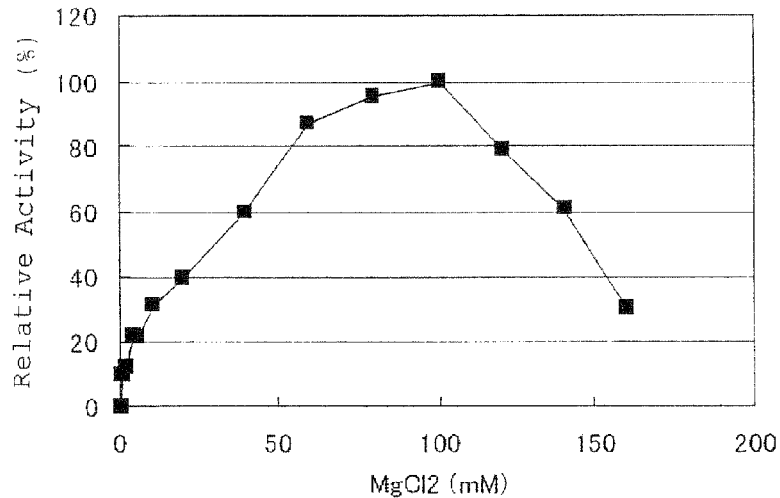
Figures 2, 13:
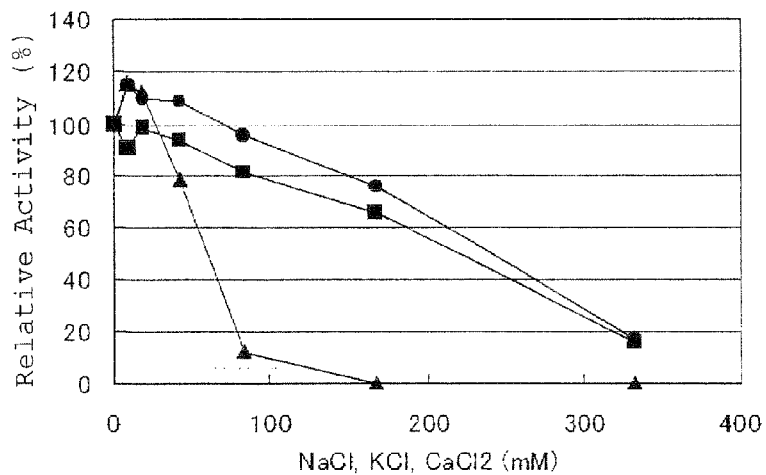
Figures 3, 13:
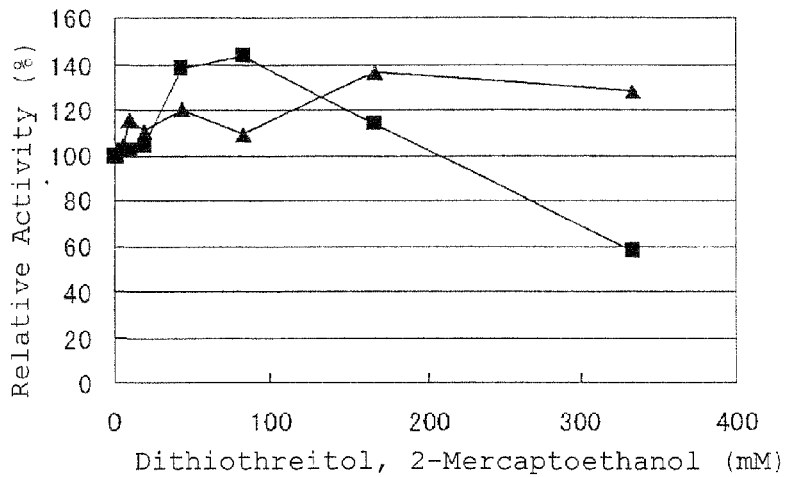
Figures 4, 13:
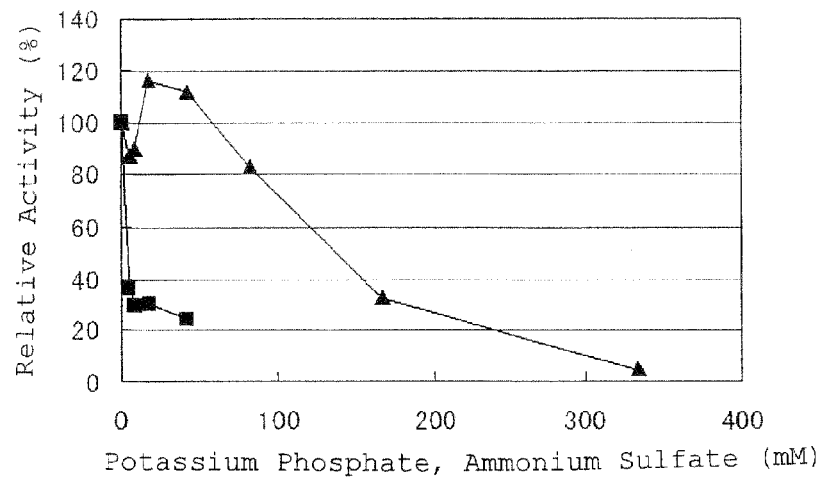

In FIG. 13-1, values are indicated defining the activity for magnesium chloride at a final concentration of 100 mM as 100.

As shown in FIG. 13-1, the optimal magnesium ion concentration of the polypeptide having an endonuclease activity of the present invention was 60 to 120 mM.

2. Influence of Sodium Ion, Potassium Ion and Calcium Ion

Influence of ion concentrations was examined by adding sodium chloride, potassium chloride or calcium chloride at a final concentration of 0, 8, 17, 42, 83, 167 or 333 mM to a reaction mixture having the above-mentioned composition. The results are shown in FIG. 13-2.

In FIG. 13-2, values are indicated defining the activity for sodium chloride, potassium chloride or calcium chloride at a final concentration of 0 mM as 100. Squares (■), circles (●) and triangles (▲) represent results for sodium chloride, potassium chloride and calcium chloride, respectively.

As shown in FIG. 13-2, high activities were observed with sodium ion or potassium ion at concentrations up to 167 mM and with calcium ion at concentrations up to 42 mM.

3. Influence of Reducing Agents

Influence of reducing agents was examined by adding dithiothreitol or 2-mercaptoethanol at a final concentration of 0, 8, 17, 42, 83, 167 or 333 mM to a reaction mixture having the above-mentioned composition. The results are shown in FIG. 13-3.

In FIG. 13-3, values are indicated defining the activity for dithiothreitol or 2-mercaptoethanol at a final concentration of 0 mM as 100. Squares (■) and triangles (▲) represent results for dithiothreitol and 2-mercaptoethanol, respectively.

As shown in FIG. 13-3, high activities were observed with dithiothreitol at concentrations up to 167 mM and with 2-mercaptoethanol at concentrations up to 333 mM.

4. Influence of Potassium Phosphate and Ammonium Sulfate

Influence of additives was examined by adding potassium phosphate or ammonium sulfate at a final concentration of 0, 4, 8, 17, 42, 83, 167 or 333 mM to a reaction mixture having the above-mentioned composition. The results are shown in FIG. 13-4.

In FIG. 13-4, values are indicated defining the activity for potassium phosphate or ammonium sulfate at a final concentration of 0 mM as 100. Squares (■) and triangles (▲) represent results for potassium phosphate or ammonium sulfate, respectively.

As shown in FIG. 13-4, a low activity was observed with potassium phosphate even at a concentration of 4 mM. Thus, it was found that a phosphate buffer is not suitable as a reaction buffer for the polypeptide having an endonuclease activity of the present invention. High activities were observed with ammonium sulfate at concentrations up to 83 mM.

(5) Viscosity Reduction Effect of Psychrophilic Microorganism-derived Endonuclease Upon Protein Extraction From *Escherichia coli* at Low Temperatures The polypeptide having an endonuclease activity prepared in Example 2(5) above was added in place of DNase I when extraction was carried out using a protein extraction reagent kit TALON xTractor Buffer Kit (Clontech), and reduction in viscosity was examined. The examination was carried out according to the protocol of TALON xTractor Buffer Kit. 128 μl of TALON xTractor Buffer, 1.28 μl of Lysozyme (50×) and one of three amounts (0.256 U, 2.56 U or 25.6 U) of DNase I or the polypeptide having an endonuclease activity of the present invention were added to 6.4 mg of wet cells of *Escherichia coli* BL21 expressing yeast AIP2 gene (GenBank Acc. No. U35667) inserted into a vector pColdTF. The mixture was reacted for 30 minutes at 30° C. or on ice.

10 μl of the reaction mixture was subjected to electrophoresis on 1% agarose gel for analysis of cleavage product. The results are shown in FIG. 14.

In addition, a sample buffer was added to the remaining extract not used for the electrophoresis on 1% agarose gel, the mixture was boiled, and a portion corresponding to 4 μl of the extract was then subjected to SDS-PAGE. The results are shown in FIG. 15.

Figure 14:
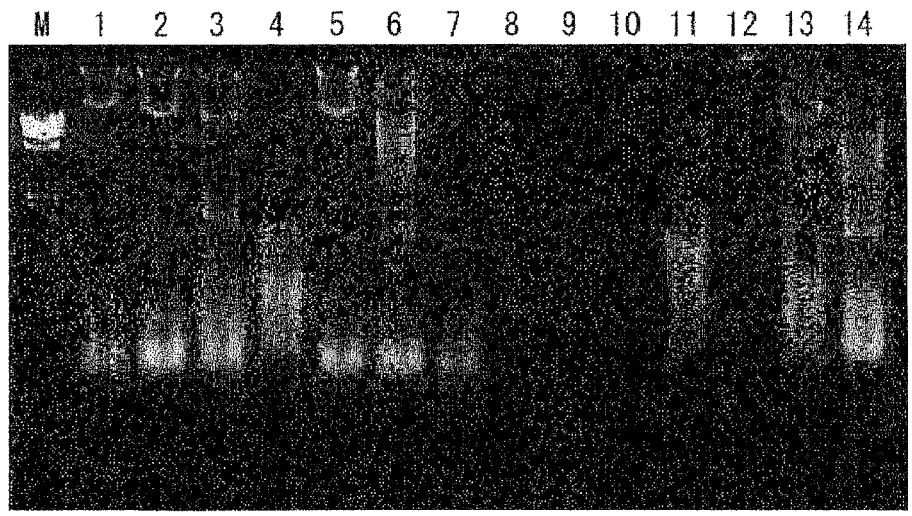
FIG. 14 illustrates results of electrophoresis showing viscosity-reducing effect upon protein extraction from *Escherichia coli* at low temperatures using the endonuclease of the present invention and DNase I.

In FIG. 14, the respective lanes represent the following: Lanes 1-7: ones reacted at 30° C.; Lanes 8-14: one reacted on ice (lanes for which no band is observed in the electrophoresis image represent results for samples which could not be appropriately applied because of failure in pipetting due to the viscosity); Lane M: λ-HindIII marker; Lanes 1 and 8: without the addition of enzyme; Lanes 2 and 9: 0.256 U of DNase I; Lanes 3 and 10: 2.56 U of DNase I; Lanes 4 and 11: 25.6 U of DNase I; Lanes 5 and 12: 0.256 U of the polypeptide having an endonuclease activity of the present invention; Lanes 6 and 13: 2.56 U of the polypeptide having an endonuclease activity of the present invention; and Lanes 7 and 14: 25.6 U of the polypeptide having an endonuclease activity of the present invention.

As shown in FIG. 14, when 2.56 U of DNase I was used for treatment on ice, viscosity remained so much that pipetting was difficult and the sample could not be appropriately applied (Lane 10). On the other hand, reduction in viscosity resulting from degradation of genomic DNA was observed using 2.56 U of the polypeptide having an endonuclease activity of the present invention (Lane 13).

Figure 15:
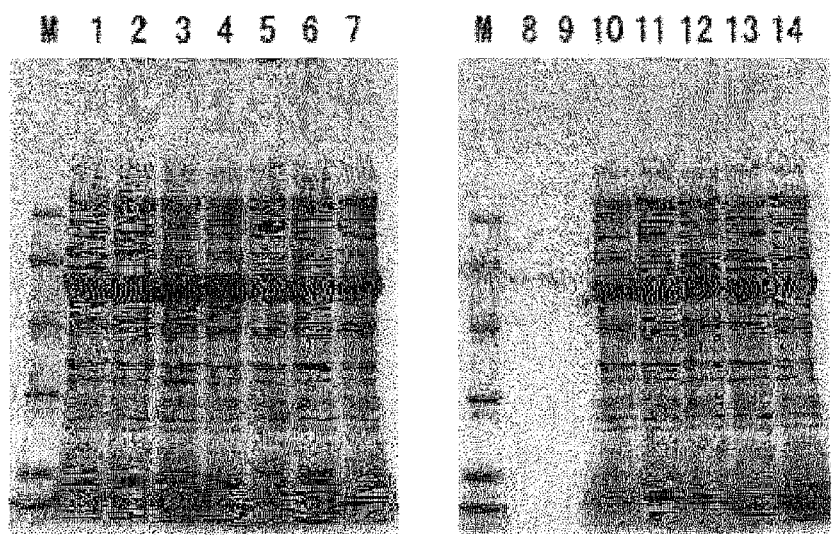
FIG. 15 illustrates results of electrophoresis showing viscosity-reducing effect upon protein extraction from *Escherichia coli* at low temperatures using the endonuclease of the present invention and DNase I.

In FIG. 15, the respective lanes represent the following: Lanes 1-7: ones reacted at 30° C.; Lanes 8-14: one reacted on ice (lanes for which no band is observed in the electrophoresis image represent results for samples which could not be appropriately applied because of failure in pipetting due to the viscosity); Lane M: molecular weight marker 97, 66, 45, 31, 21, 14 KDa; Lanes 1 and 8: without the addition of enzyme;

Lanes 2 and 9: 0.256 U of DNase I; Lanes 3 and 10: 2.56 U of DNase I; Lanes 4 and 11: 25.6 U of DNase I; Lanes 5 and 12: 0.256 U of the polypeptide having an endonuclease activity of the present invention; Lanes 6 and 13: 2.56 U of the polypeptide having an endonuclease activity of the present invention; and Lanes 7 and 14: 25.6 U of the polypeptide having an endonuclease activity of the present invention.

As shown in FIG. 15, when 0.256 U of DNase I was used for treatment on ice, viscosity remained so much that pipetting was difficult and the sample could not be appropriately applied (Lane 9). On the other hand, the sample could be appropriately applied using 0.256 U of the polypeptide having an endonuclease activity of the present invention (Lane 12), and reduction in viscosity resulting from degradation of genomic DNA was observed with the addition of an amount less by one order of magnitude than DNase I.

Based on the above, it was confirmed that viscosity could be reduced by treatment on ice using the polypeptide having an endonuclease activity of the present invention without influencing the protein of interest observed as a main band.

(6) Degradation of Genomic DNA in Supernatant of Sonicated *Escherichia coli* Using Psychrophilic Microorganism-derived Endonuclease The polypeptide having an endonuclease activity prepared in Example 2(5) above or DNase I (Takara Bio) was added to a supernatant of sonicated *Escherichia coli* and amounts of remaining *Escherichia coli*-derived genome were compared with each other.

10 mM tris-hydrochloride buffer (pH 7.5) and 10 mM magnesium chloride was added to cells of *Escherichia coli* BL21 expressing yeast AIP2 gene inserted into a vector pColdTF (5 ml of buffer per 1 g of wet cells), and the homogenate supernatant was diluted 50-fold with the buffer. One of three amounts (0.1 U, 1 U or 10 U) of DNase I or the polypeptide having an endonuclease activity of the present invention was added to 50 µl of the diluted supernatant. The mixture was reacted at 30° C. or on ice. After 30 minutes or 2 hours, 10 µl of the reaction mixture was subjected to electrophoresis on 1% agarose gel for analysis of cleavage product. The results obtained after reaction for 30 minutes are shown in FIG. 16, and the results obtained after reaction for 2 hours are shown in FIG. 17.

Figure 16:
FIG. 16 illustrates results of comparative test for *Escherichia coli* genomic DNA degradation reaction between the endonuclease of the present invention and DNase I.
Figure 17:
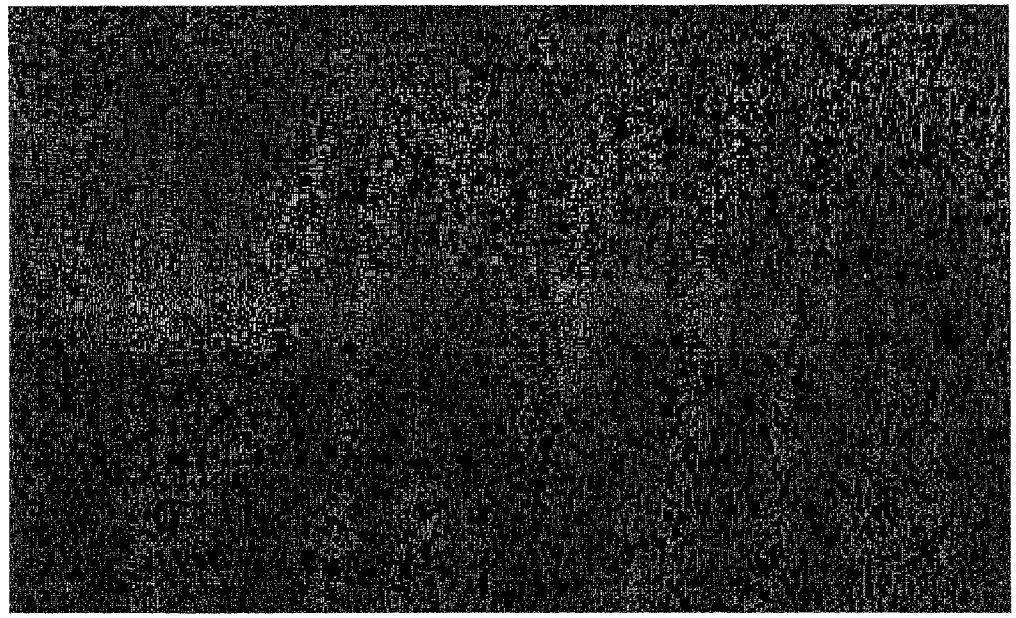
FIG. 17 illustrates results of comparative test for *Escherichia coli* genomic DNA degradation reaction between the endonuclease of the present invention and DNase I.

In FIGS. 16 and 17, the respective lanes represent the following: Lanes 1-7: ones reacted at 30° C.; Lanes 8-14: one reacted on ice; Lane M: λ-HindIII marker; Lanes 1 and 8: without the addition of enzyme; Lanes 2 and 9: 0.1 U of DNase I; Lanes 3 and 10: 1 U of DNase I; Lanes 4 and 11: 10 U of DNase I; Lanes 5 and 12: 0.1 U of the polypeptide having an endonuclease activity of the present invention; Lanes 6 and 13: 1 U of the polypeptide having an endonuclease activity of the present invention; and Lanes 7 and 14: 10 U of the polypeptide having an endonuclease activity of the present invention.

By comparing the results in FIGS. 16 and 17 for reaction on ice with DNase I (Lanes 10 and 11) with those with the polypeptide having an endonuclease activity of the present invention (Lanes 13 and 14), it was confirmed that degradation of genomic DNA proceeded better using the polypeptide having an endonuclease activity of the present invention.

Based on the above, it was confirmed that the polypeptide having an endonuclease activity of the present invention could be used to degrade DNA in a reaction at a low temperature without influencing the protein of interest.

INDUSTRIAL APPLICABILITY

The present invention provides a polypeptide having an endonuclease activity which is useful for elimination of contamination upon PCR, elimination of genome upon RT-PCR, elimination of nucleic acids from protein solutions or reduction in viscosity of protein extracts, and a gene encoding the polypeptide.

Sequence Listing Free Text

SEQ ID NO:1; A sequence of designed oligonucleotide PCR primer for amplifying a gene of encoding DNase. "nucleotide 4 to 9 is EcoRI restriction site."

SEQ ID NO:2; A sequence of designed oligonucleotide PCR primer for amplifying a gene of encoding DNase. "nucleotide 4 to 9 is BamHI restriction site."

SEQ ID NO:5; A sequence of artificial protein comprising Perfect DB sequence, His Tag sequence, Factor Xa sequence and linker, and DNase.

SEQ ID NO:6; A sequence of a gene encoding an artificial protein comprising Perfect DB sequence, His Tag sequence, Factor Xa sequence and linker, and DNase.

SEQ ID NO:7; A sequence of designed oligonucleotide PCR primer for amplifying a gene of encoding DNase. "nucleotide 4 to 9 is NdeI restriction site."

SEQ ID NO:8; A sequence of artificial protein comprising Perfect DB sequence, His Tag sequence, Trigger Factor sequence, HRV 3C sequence, Thrombin sequence, Factor Xa sequence and linker, and endonuclease.

SEQ ID NO:9; A sequence of a gene encoding an artificial protein comprising Perfect DB sequence, His Tag sequence, Trigger Factor sequence, HRV 3C sequence, Thrombin sequence, Factor Xa sequence and linker, and endonuclease.

The invention claimed is:

1. An isolated and purified polypeptide having endonuclease activity, which is selected from the group consisting of the following:
(a) a polypeptide having the amino acid sequence of SEQ ID NO:10; and
(b) a polypeptide having an amino acid sequence that shares at least 90% sequence homology to the amino acid sequence of SEQ ID NO:10.

2. The polypeptide of claim 1, which has at least the following physical and chemical properties (a) and (b):
(a) substrate specificity: acting on linear double-stranded DNA, circular double-stranded DNA, single-stranded DNA and RNA; and
(b) reactivity at low temperatures: retaining, at 0 to 10° C., 30% or more of its activity at 20° C.

* * * * *